(12) United States Patent　　　　(10) Patent No.:　US 12,618,097 B2

Zhang et al.　　　　　　　　　　　　(45) Date of Patent:　May 5, 2026

---

(54) METHOD FOR DETERMINING LONG NON-CODING RIBONUCLEIC ACID INTERACTION PROTEINS

(71) Applicant: City University of Hong Kong, Kowloon (HK)

(72) Inventors: Liang Zhang, New Territories (HK); Jian Yan, Kowloon (HK); Jingyu Li, Kowloon (HK); Wenkai Yi, New Territories (HK); Ligang Fan, Kowloon (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 17/240,009

(22) Filed: Apr. 26, 2021

(65) Prior Publication Data

US 2021/0340592 A1　　Nov. 4, 2021

(30) Foreign Application Priority Data

Apr. 30, 2020　(CN) .......................... 202010367970.0

(51) Int. Cl.
| | |
|---|---|
| *C12N 9/12* | (2006.01) |
| *C12N 9/00* | (2006.01) |
| *C12N 9/22* | (2006.01) |
| *C12N 15/11* | (2006.01) |
| *C12Q 1/25* | (2006.01) |
| *G16B 40/00* | (2019.01) |

(52) U.S. Cl.
CPC ................. *C12Q 1/25* (2013.01); *C12N 9/22* (2013.01); *C12N 9/93* (2013.01); *C12N 15/11* (2013.01); *G16B 40/00* (2019.02); *C12N 2310/20* (2017.05); *G01N 2440/32* (2013.01)

(58) Field of Classification Search
None
See application file for complete search history.

(56) References Cited

U.S. PATENT DOCUMENTS 10,476,825 B2 * 11/2019 Hsu ......................... C12N 15/85

FOREIGN PATENT DOCUMENTS

WO　　WO-2021089984 A1 * 5/2021 ............... C12N 9/22

OTHER PUBLICATIONS

Silvana Konermann et al (Transcriptome Engineering with RNA-Targeting Type VI-D Crispr Effectors. Cell 173, 665-676, Apr. 19, 2018). (Year: 2018).*
Muthukumar Ramanathan et al (RNA-protein interaction detection in living cells Nature Methods | vol. 15 No. 3 | Mar. 2018 | 207-212). (Year: 2018).*
Shuai Zhen et al. (Application of CRISPR-Cas9 for Long Noncoding RNA Genes in Cancer Research. Human Gene Therapy. vol. 30, Jan. 2019.3-9. (Year: 2019).*
Muthukumar Ramanathan RNA-protein interaction detection in living cells. Nature Methods | vol. 15 No. 3 | Mar. 2018 | 207-212). (Year: 2018).*
Yi et al. , Nature Methods, vol. 17, pp. 685-688, Jul. 2020.*
Konermann et al., "Transcriptome Engineering with RNA-Targeting Type VI-D CRISPR Effectors"2018, Cell 173, 1-12.
Ma, Hongming et al., "Pol III Promoters to Express Small RNAs: Delineation of Transcription Initiation" Molecular Therapy—Nucleic Acids (2014) 3, e161.
Kim, Sinae et al., "Efficiency of the Elongation Factor-1_ Promoter in Mammalian Embryonic Stem Cells Using Lentiviral" Stem Cells and Development 16:537-545 (2007) DOI: 10.1089/scd.2006.0088.
Lambeth, Luke S et al., "Characterisation and application of a bovine U6 promoter for expression of short hairpin RNAs" BMC Biotechnology 2005, 5:13 doi:10.1186/1472-6750-5-13.

* cited by examiner

*Primary Examiner* — Richard G Hutson
(74) *Attorney, Agent, or Firm* — Renner, Kenner, Greive, Bobak, Taylor & Weber

(57)　　　　ABSTRACT

The present invention provides a novel method for determining a long-chain non-coding ribonucleic acid interaction protein. The present invention provides a fusion protein formed by BASU and dCasRx, a mammalian expression vector for expressing said fusion protein. The method for determining the lncRNA interaction protein according to the present invention comprises: co-transfecting a mammalian expression vector that expresses the fusion protein and a gRNA that specifically targets the target lncRNA into target cells, thereby BASU specifically biotin-labeling effector proteins nearby; isolating the biotinylated proteins by using a streptavidin affinity coupled magnetic bead and then eluting, and digesting by trypsin and quantitatively analyzing by a label-free mass spectrometry. The present invention can highly credibly determine the proteins that interact with lncRNA.

5 Claims, 15 Drawing Sheets
(15 of 15 Drawing Sheet(s) Filed in Color)

Specification includes a Sequence Listing.

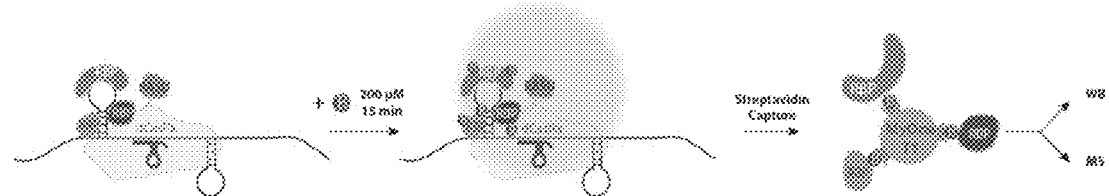
Figure 1a
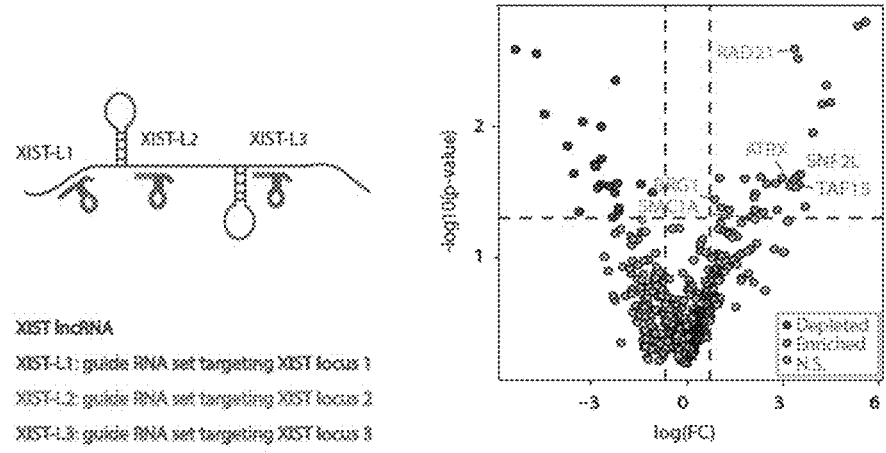
Figure 1b
Figure 1c
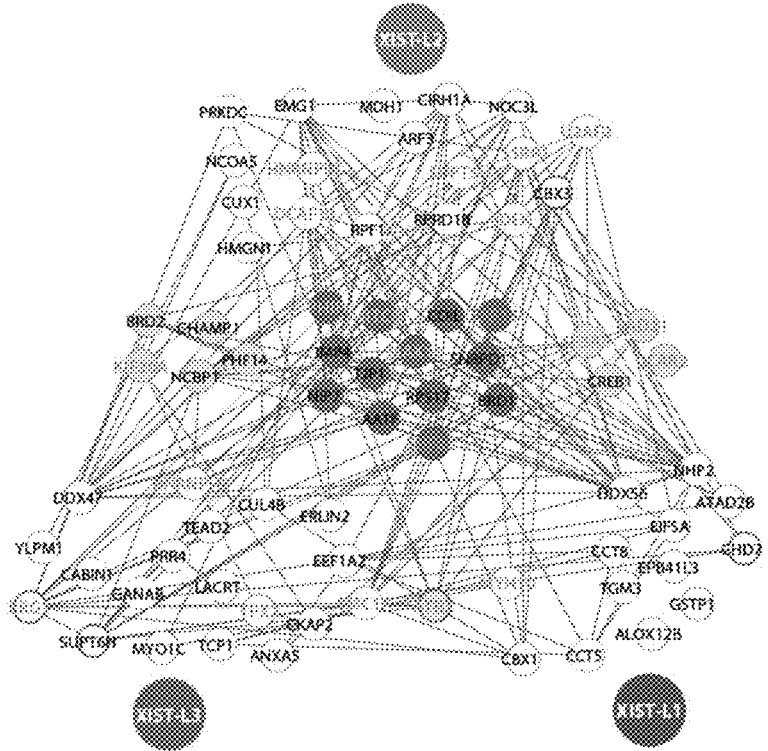
Figure 1d

| GO term | p Value | Genes Involved |
|---------|---------|----------------|
| Covalent Chromatin Modification | 6.0e-5 | ATRX, SNF2L, BRG1, BRD2, CHD7 |
| Chromatin Remodeling | 5.8e-4 | ATRX, SNF2L, BRG1, CHD7 |
| Positive Regulation of Transcription | 2.1e-3 | ATRX, RAD21, BRG1, AATF, CREB1, CHD7, CKAP2, PHIP |
| RNA splicing | 3.8e-3 | CCAR2, NCBP1, SNRPD1, SF3A3 |
| RNA Maturation | 2.8e-2 | MAK16, NHP2 |
Figure 1e
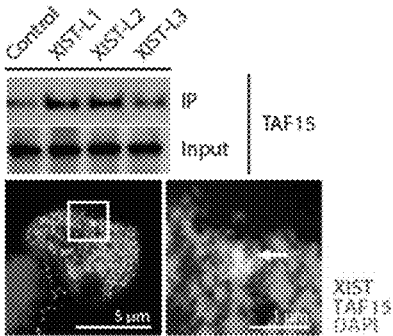
Figure 2a
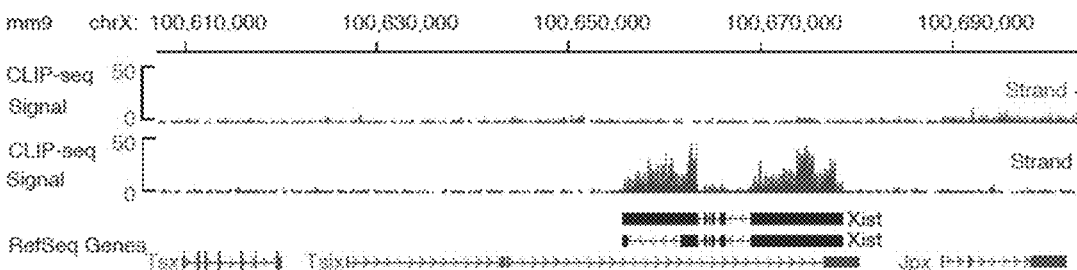
Figure 2b
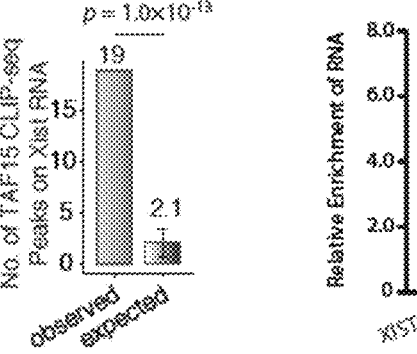
Figure 2c
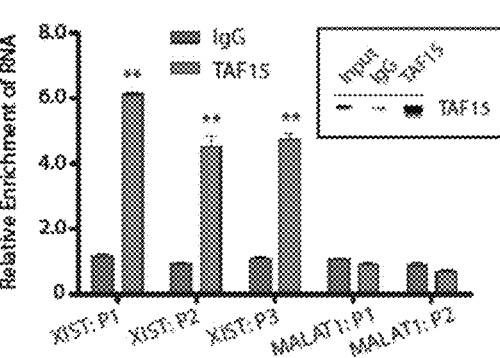
Figure 2d

Figure 2f                                                    Figure 2g

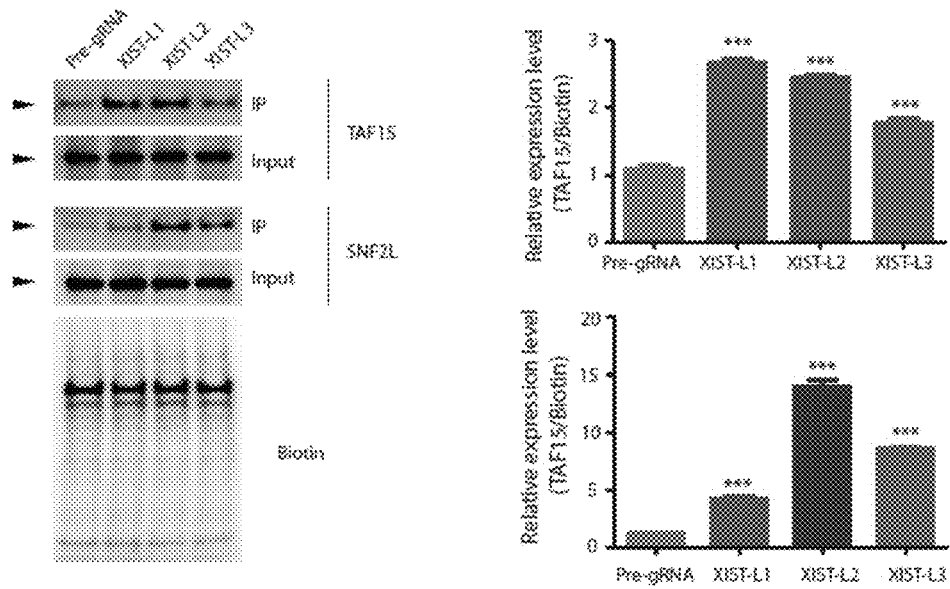
Figure 7
*Oligo Design*
Figure 8a
*Experimental Procesure(RNA-SELEX)*
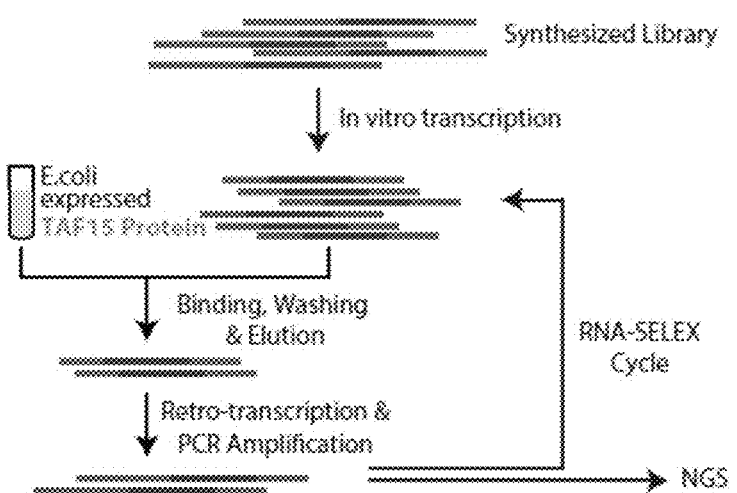
Figure 8b

*TAF15-HTR-SELEX*

*Machine Learning - Data Analysis*

| GO term | p Value | Genes Involved |
|---|---|---|
| Extracellular Exosome | 4.9e-5 | FKBP4, ACTN4, ANXA5, CCT7, DLG1, EZR, FLNB, GJA1, GPI, KRT13, MDH2, PEBP1, PAICS, PDIA6, STX3, TCP1, TPI1 |
| Stress Fibre | 3.0e-3 | LIMA1, ACTN4, FLNB, SIPA1L3 |
| Brush Border | 2.3e-3 | LIMA1, ACTN4, EZR, FLNB |
| Myelin Sheath | 3.1e-3 | EZR, GPI, MDH2, STIP1, TCP1 |
| Focal Adhesion | 4.8e-3 | LIMA1, ACTN4, ANXA5, EZR, FLNB, GJA1 |
| Actin Filament | 3.3e-2 | FYN, EZR, PLS3 |
Figure 10d
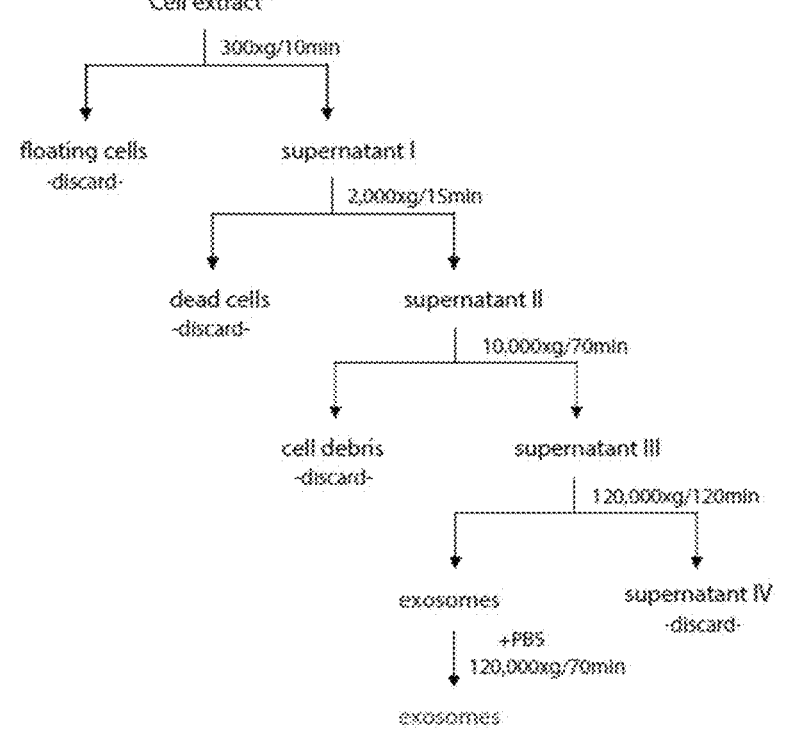
Figure 11a
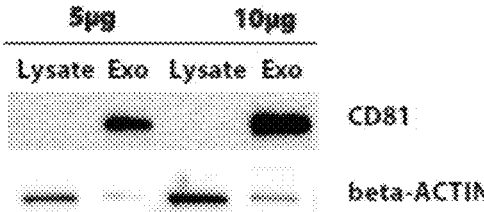
Figure 11b

SEQUENCE LISTING

<160> NUMBER OF SEQ ID NOS: 18

<210> SEQ ID NO 1
<211> LENGTH: 30
<212> TYPE: DNA
<213> ORGANISM: Artificial Sequence
<220> FEATURE:
<223> OTHER INFORMATION: gRNA

<400> SEQUENCE: 1
tgaaaagacc ttgaaaacac ctggtgtacc                                30

<210> SEQ ID NO 2
<211> LENGTH: 30
<212> TYPE: DNA
<213> ORGANISM: Artificial Sequence -continued

```
<220> FEATURE:
<223> OTHER INFORMATION: gRNA

<400> SEQUENCE: 2
aggaggggac aaataagagg ggacagaggt                                      30

<210> SEQ ID NO 3
<211> LENGTH: 30
<212> TYPE: DNA
<213> ORGANISM: Artificial Sequence
<220> FEATURE:
<223> OTHER INFORMATION: gRNA

<400> SEQUENCE: 3
tatgtggaga ggaccctcct tttctagtgc                                      30

<210> SEQ ID NO 4
<211> LENGTH: 30
<212> TYPE: DNA
<213> ORGANISM: Artificial Sequence
<220> FEATURE:
<223> OTHER INFORMATION: gRNA

<400> SEQUENCE: 4
agtcttatgg agtgggcact ccctgctgga                                      30

<210> SEQ ID NO 5
<211> LENGTH: 30
<212> TYPE: DNA
<213> ORGANISM: Artificial Sequence
<220> FEATURE:
<223> OTHER INFORMATION: gRNA

<400> SEQUENCE: 5
agtagagggg ttcatgtata atgggtggga                                      30

<210> SEQ ID NO 6
<211> LENGTH: 30
<212> TYPE: DNA
<213> ORGANISM: Artificial Sequence
<220> FEATURE:
<223> OTHER INFORMATION: gRNA

<400> SEQUENCE: 6
agaaggggct ttgggtagtc agcatactca                                      30

<210> SEQ ID NO 7
<211> LENGTH: 30
<212> TYPE: DNA
<213> ORGANISM: Artificial Sequence
<220> FEATURE:
<223> OTHER INFORMATION: gRNA

<400> SEQUENCE: 7
taagagacga actcctggag ctcaaggtcg                                      30

<210> SEQ ID NO 8
<211> LENGTH: 30
<212> TYPE: DNA
<213> ORGANISM: Artificial Sequence
<220> FEATURE:
<223> OTHER INFORMATION: gRNA

<400> SEQUENCE: 8
gctgcctcag ttcttagcgc aggttgacaa                                      30
```

-continued

```
<210> SEQ ID NO 9
<211> LENGTH: 30
<212> TYPE: DNA
<213> ORGANISM: Artificial Sequence
<220> FEATURE:
<223> OTHER INFORMATION: gRNA

<400> SEQUENCE: 9
ttcctattgt aactgaaggg atagttggct                                                  30

<210> SEQ ID NO 10
<211> LENGTH: 30
<212> TYPE: DNA
<213> ORGANISM: Artificial Sequence
<220> FEATURE:
<223> OTHER INFORMATION: gRAN

<400> SEQUENCE: 10
ccaaatatgc gtactaactt gtagcaacca                                                  30

<210> SEQ ID NO 11
<211> LENGTH: 30
<212> TYPE: DNA
<213> ORGANISM: Artificial Sequence
<220> FEATURE:
<223> OTHER INFORMATION: gRNA

<400> SEQUENCE: 11
agttgcgggg ccccagtcct ttacagaagt                                                  30

<210> SEQ ID NO 12
<211> LENGTH: 30
<212> TYPE: DNA
<213> ORGANISM: Artificial Sequence
<220> FEATURE:
<223> OTHER INFORMATION: gRNA

<400> SEQUENCE: 12
ttctgcgttg ctaaaatggc gctgcgctta                                                  30

<210> SEQ ID NO 13
<211> LENGTH: 30
<212> TYPE: DNA
<213> ORGANISM: Artificial Sequence
<220> FEATURE:
<223> OTHER INFORMATION: gRNA

<400> SEQUENCE: 13
aatcttagaa acgtgaaaac ccactcttgg                                                  30

<210> SEQ ID NO 14
<211> LENGTH: 30
<212> TYPE: DNA
<213> ORGANISM: Artificial Sequence
<220> FEATURE:
<223> OTHER INFORMATION: gRNA

<400> SEQUENCE: 14
ttgctttttt gttcgagaaa tcggagcagc                                                  30

<210> SEQ ID NO 15
<211> LENGTH: 12356
<212> TYPE: DNA
<213> ORGANISM: Artificial Sequence
<220> FEATURE:
<223> OTHER INFORMATION: BASU RaPID plasmid (AddgeneNo. 107250)
```

```
                 containing BASU gene
<220> FEATURE:
<221> NAME/KEY: gene
<222> LOCATION: (3602)..(4381)
<223> OTHER INFORMATION: Basu gene
<220> FEATURE:
<221> NAME/KEY: misc_feature
<222> LOCATION: (4366)..(4366)
<223> OTHER INFORMATION: n is a, c, g, or t

<400> SEQUENCE: 15
ttcactccca aagaagacaa gatatccttg atctgtggat ctaccacaca caaggctact      60
tccctgatta gcagaactac acaccagggc caggggtcag atatccactg acctttggat     120
ggtgctacaa gctagtacca gttgagccag ataaggtaga agaggccaat aaaggagaga     180
acaccagctt gttacaccct gtgagcctgc atgggatgga tgacccggag agagaagtgt     240
tagagtggag gtttgacagc cgcctagcat ttcatcacgt ggcccgagag ctgcatccgg     300
agtacttcaa gaactgctga tatcgagctt gctacaaggg actttccgct ggggactttc     360
cagggaggcg tggcctgggc gggactgggg agtggcgagc cctcagatcc tgcatataag     420
cagctgcttt ttgcctgtac tgggtctctc tggttagacc agatctgagc ctgggagctc     480
tctggctaac tagggaaccc actgcttaag cctcaataaa gcttgccttg agtgcttcaa     540
gtagtgtgtg cccgtctgtt gtgtgactct ggtaactaga gatccctcag acccttttag     600
tcagtgtgga aaatctctag cagtggcgcc cgaacaggga cttgaaagcg aaagggaaac     660
cagaggagct ctctcgacgc aggactcggc ttgctgaagc gcgcacggca agaggcgagg     720
ggcggcgact ggtgagtacg ccaaaaattt tgactagcgg aggctagaag agagagatg      780 ggtgcgagag cgtcagtatt aagcgggggga gaattagatc gcgatgggaa aaaattcggt     840
taaggccagg gggaagaaa aaatataaat taaaacatat agtatgggca agcagggagc     900
tagaacgatt cgcagttaat cctggcctgt tagaaacatc agaaggctgt agacaaatac     960
tgggacagct acaaccatcc cttcagacag gatcagaaga acttagatca ttatataata    1020
cagtagcaac cctctattgt gtgcatcaaa ggatagagat aaaagacacc aaggaagctt    1080
tagacaagat agaggaagag caaaacaaaa gtaagaccac cgcacagcaa gcggccggcc    1140
gctgatcttc agacctggag gaggagatat gagggacaat tggagaagtg aattatataa    1200
atataaagta gtaaaaattg aaccattagg agtagcaccc accaaggcaa agagaagagt    1260
ggtgcagaga gaaaaaagag cagtgggaat aggagctttg ttccttgggt tcttgggagc    1320
agcaggaagc actatgggcg cagcgtcaat gacgctgacg gtacaggcca gacaattatt    1380
gtctggtata gtgcagcagc agaacaattt gctgagggct attgaggcgc aacagcatct    1440
gttgcaactc acagtctggg gcatcaagca gctccaggca agaatcctgg ctgtggaaag    1500
atacctaaag gatcaacagc tcctggggat ttggggttgc tctggaaaac tcatttgcac    1560
cactgctgtg ccttggaatg ctagttggag taataaatct ctggaacaga tttggaatca    1620
cacgacctgg atggagtggg acagagaaat taacaattac acaagcttaa tacactcctt    1680
aattgaagaa tcgcaaaacc agcaagaaaa gaatgaacaa gaattattgg aattagataa    1740
atgggcaagt ttgtggaatt ggtttaacat aacaaattgg ctgtggtata taaaattatt    1800
cataatgata gtaggaggct tggtaggttt aagaatagtt tttgctgtac tttctatagt    1860
gaatagagtt aggcagggat attcaccatt atcgtttcag acccacctcc caaccccgag    1920
gggacccgac aggcccgaag gaatagaaga agaaggtgga gagagagaca gagacagatc    1980
cattcgatta gtgaacggat cggcactgcg tgcgccaatt ctgcagacaa atggcagtat    2040
```

-continued

```
tcatccacaa ttttaaaaga aaaggggggga ttgggggggta cagtgcaggg gaaagaatag    2100
tagacataat agcaacagac atacaaacta aagaattaca aaaacaaatt acaaaaattc    2160
aaaattttcg ggtttattac agggacagca gagatccagt ttggttagta ccgggcccgc    2220
tctagtccgg aatcagtcct gctcctcggc cacgaagtgc acgcagttgc cggccgggtc    2280
gcgcagggcg aactcccgcc cccacggctg ctcgccgatc tcggtcatgg ccggcccgga    2340
ggcgtcccgg aagttcgtgg acacgacctc cgaccactcg gcgtacagct cgtccaggcc    2400
gcgcacccac acccaggcca gggtgttgtc cggcaccacc tggtcctgga ccgcgctgat    2460
gaacagggtc acgtcgtccc ggaccacacc ggcgaagtcg tcctccacga agtcccggga    2520
gaacccgagc cggtcggtcc agaactcgac cgctccggcg acgtcgcgcg cggtgagcac    2580
cggaacggca ctggtcaact tggccatggt ggccctccta tagtgagtcg tattatacta    2640
tgccgatata ctatgccgat gattaattgt caacacgtgc tgcaggtccg aggttctaga    2700
cgtattaccg ccatgcatta gttattaata gtaatcaatt acggggtcat tagttcatag    2760
cccatatatg gagttccgcg ttacataact tacggtaaat ggcccgcctg gctgaccgcc    2820
caacgacccc cgcccattga cgtcaataat gacgtatgtt cccatagtaa cgccaatagg    2880
gactttccat tgacgtcaat gggtggagta tttacggtaa actgcccact tggcagtaca    2940
tcaagtgtat catatgccaa gtacgccccc tattgacgtc aatgacggta aatggcccgc    3000
ctggcattat gcccagtaca tgaccttatg ggactttcct acttggcagt acatctacgt    3060
attagtcatc gctattacca tggtgatgcg gttttggcag tacatcaatg ggcgtggata    3120
gcggtttgac tcacggggat ttccaagtct ccaccccatt gacgtcaatg ggagtttgtt    3180
ttggcaccaa aatcaacggg actttccaaa atgtcgtaac aactccgccc cattgacgca    3240
aatgggcggt aggcgtgtac ggtgggaggt ctatataagc agagctcgtt tagtgaaccg    3300
tcagatcgcc tggagacgcc atccacgctg ttttgacctc catagaagac accgactcta    3360
ctagaggatc catgaacgca cgaacacgac gacgtgagcg tcgcgctgag aaacaagctc    3420
aatggaaagc tgcaaactca ggaggcggtg ggtctggtgg cgggagcggc cgcctgcagc    3480 tgcccccccct ggagcgcctg accctggacc tcgagtaccc atacgatgtg cctgactatg    3540
ctggcaagtt gtctgaatca gagattaggt ttggactgaa aacggaggtg atgggccaac    3600
atcttatcta tcacgatgtt ttgtccagca cacaaaagac agcccatgaa ttggcaaata    3660
acaatgcccc cgagggtacc ctcgtggttg cagataaaca gacagccggt aggggcggga    3720
tgagccgagt gtggcattct caagaaggaa acggagtatg gatgagtttg atattgcgcc    3780
cggacattcc gctccaaaag acgccccaac ttaccttgct ggcagctgta gcggtggttc    3840
agggaataga agaggccgcg ggcatacaga ctgatataaa gtggccgaac gacatactca    3900
ttaacgggaa aaaaacagta gggatactta ccgaaatgca agctgaggag gatcgagtgc    3960
gctccgtgat tattggtatt ggcattaatg taaatcagca acccaatgat ttccccgatg    4020
agctcaagga cattgcgacg agtctgtccc aggcagctgg ggaaaagatc gacagggcag    4080
gtgtaatcca gcatatcttg ctttgtttcg aaaagcgata ccgagactac atgacccacg    4140
gtttcacgcc catcaagctc ttgtgggagt catacgccct cggtattggc acgaacatga    4200
gggcgagaac tctcaacggg acattttacg gtaaggcgtt gggtattgac gacgaagggg    4260 tactttttgtt ggaaactaat gaaggcatta agaagatata cagcgcggac atcagcctta    4320
ggtgaacgcg tctggccacc ggtcgcccct ctccctcccc ccccctaac gttactggcc    4380
```

-continued

```
gaagccgctt ggaataaggc cggtgtgcgt ttgtctatat gttattttcc accatattgc   4440
cgtcttttgg caatgtgtgg gcccggaaac ctggccctgt cttcttgacg agcattccta   4500
ggggtctttc ccctctcgcc aaaggaatgc aaggtctgtt gaatgtcgtg aaggaagcag   4560
ttcctctgga agcttcttga agacaaacaa cgtctgtagc gacccttgc aggcagcgga    4620 accccccacc tggcgacagg tgcctctgcg gccaaaagcc acgtgtataa gatacacctg   4680
caaaggcggc acaaccccag tgccacgttg tgagttggat agttgtggaa agagtcaaat   4740
ggctctcctc aagcgtattc aacaaggggc tgaaggatgc ccagaaggta ccccattgta   4800
tgggatctga tctggggcct cggtgcacat gctttacatg tgtttagtcg aggttaaaaa   4860
aacgtctagg cccccgaac cacggggacg tggttttcct ttgaaaaaca cgataatacc    4920
atggccaccg agtacaagcc cacggtgcgc ctcgccaccc gcgacgacgt ccccgggcc    4980 gtacgcaccc tcgccgccgc gttcgccgac taccccgcca cgcgccacac cgtcgacccg   5040
gaccgccaca tcgagcgggt caccgagctg caagaactct tcctcacgcg cgtcgggctc   5100
gacatcggca aggtgtgggt cgcggacgac ggcgccgcgg tggcggtctg gaccacgccg   5160
gagagcgtcg aagcggggc ggtgttcgcc gagatcggcc cgcgcatggc cgagttgagc   5220
ggttcccggc tggccgcgca gcaacagatg gaaggcctcc tggcgccgca ccggcccaag   5280
gagcccgcgt ggttcctggc caccgtcggc gtatcgcccg accaccaggg caagggtctg   5340
ggcagcgccg tcgtgctccc cggagtggag gcggccgagc gcgccggggt gcccgccttc   5400
ctggagacct ccgcgccccg caacctcccc ttctacgagc ggctcggctt caccgtcacc   5460
gccgacgtcg aggtgcccga aggaccgcgc acctggtgca tgacccgcaa gcccggtgcc   5520
ggatcgggag agggcagagg aagtctgcta acatgcggtg acgtcgagga gaatcctggc   5580
ccaccggtcg ccaccatggt gagcaagggc gaggaggata acatggccat catcaaggag   5640
ttcatgcgct tcaaggtgca catggagggc tccgtgaacg gccacgagtt cgagatcgag   5700 ggcgagggc agggccgccc ctacgagggc acccagaccg ccaagctgaa ggtgaccaag   5760 ggtggcccc tgcccttcgc ctgggacatc ctgtcccctc agttcatgta cggctccaag   5820
gcctacgtga agcaccccgc cgacatcccc gactacttga agctgtcctt ccccgagggc   5880
ttcaagtggg agcgcgtgat gaacttcgag gacggcggcg tggtgaccgt gacccaggac   5940
tcctccctgc aggacggcga gttcatctac aaggtgaagc tgcgcggcac caacttcccc   6000
tccgacggcc ccgtaatgca gaagaagacc atgggctggg aggcctcctc cgagcggatg   6060
taccccgagg acggcgccct gaagggcgag atcaagcaga ggctgaagct gaaggacggc   6120
ggccactacg acgctgaggt caagaccacc tacaaggcca agaagcccgt gcagctgccc   6180
ggcgcctaca cgtcaacat caagttggac atcacctccc acaacgagga ctacaccatc   6240
gtggaacagt acgaacgcgc cgagggccgc cactccaccg gcggcatgga cgagctgtac   6300
aagtaagaat tcgttaacaa tcaacctctg gattacaaaa tttgtgaaag attgactggt   6360
attcttaact atgttgctcc ttttacgcta tgtggatacg ctgctttaat gcctttgtat   6420
catgctattg cttcccgtat ggctttcatt ttctcctcct tgtataaatc ctggttgctg   6480
tctctttatg aggagttgtg gcccgttgtc aggcaacgtg gcgtggtgtg cactgtgttt   6540
gctgacgcaa ccccactgg ttggggcatt gccaccacct gtcagctcct ttccgggact   6600
ttcgctttcc cctccctat tgccacggcg gaactcatcg ccgcctgcct tgcccgctgc   6660
tggacagggg ctcggctgtt gggcactgac aattccgtgg tgttgtcggg gaagctgacg   6720
tcctttccat ggctgctcgc ctgtgttgcc acctggattc tgcgcgggac gtccttctgc   6780
```

-continued

```
tacgtccctt cggccctcaa tccagcggac cttccttccc gcggcctgct gccggctctg   6840
cggcctcttc cgcgtcttcg ccttcgccct cagacgagtc ggatctccct ttgggccgcc   6900
tccccgcctg gaattaattc tgcagtcgag acctagaaaa acatggagca atcacaagta   6960
gcaatacagc agctaccaat gctgattgtg cctggctaga agcacaagag gaggaggagg   7020 tgggtttttcc agtcacacct caggtacctt taagaccaat gacttacaag gcagctgtag   7080
atcttagcca cttttttaaaa gaaagagggg gactggaagg gctaattcac tcccaacgaa   7140
gacaagatct gcttttttgct tgtactgggt ctctctggtt agaccagatc tgagcctggg   7200
agctctctgg ctaactaggg aacccactgc ttaagcctca ataaagcttg ccttgagtgc   7260
ttcaagtagt gtgtgcccgt ctgttgtgtg actctggtaa ctagagatcc ctcagaccct   7320
tttagtcagt gtggaaaatc tctagcagta gtagttcatg tcatcttatt attcagtatt   7380
tataacttgc aaagaaatga atatcagaga gtgagaggcc ttgacattgt ttaaacccgc   7440
tgatcagcct cgactgtgcc ttctagttgc cagccatctg ttgtttgccc ctcccccgtg   7500
ccttccttga ccctggaagg tgccactccc actgtccttt cctaataaaa tgaggaaatt   7560
gcatcgcatt gtctgagtag gtgtcattct attctggggg gtggggtggg gcaggacagc   7620
aagggggagg attgggaaga caatagcagg catgctgggg atgcggtggg ctctatggct   7680
tctgaggcgg aaagaaccag ctggggctct aggggggtatc cccacgcgcc ctgtagcggc   7740
gcattaagcg cggcgggtgt ggtggttacg cgcagcgtga ccgctacact tgccagcgcc   7800
ctagcgcccg ctcctttcgc tttcttccct tcctttctcg ccacgttcgc cggctttccc   7860
cgtcaagctc taaatcgggg gctcccttta gggttccgat ttagtgcttt acggcacctc   7920 gacccccaaaa aacttgatta gggtgatggt tcacgtagtg ggccatcgcc ctgatagacg   7980
gtttttcgcc ctttgacgtt ggagtccacg ttctttaata gtggactctt gttccaaact   8040
ggaacaacac tcaaccctat ctcggtctat tctttttgatt tataagggat tttgccgatt   8100
tcggcctatt ggttaaaaaa tgagctgatt taacaaaaat ttaacgcgaa ttaattctgt   8160
ggaatgtgtg tcagttaggg tgtggaaagt ccccaggctc cccagcaggc agaagtatgc   8220
aaagcatgca tctcaattag tcagcaacca ggtgtggaaa gtccccaggc tccccagcag   8280
gcagaagtat gcaaagcatg catctcaatt agtcagcaac catagtcccg cccctaactc   8340
cgcccatccc gcccctaact ccgcccagtt ccgcccattc tccgccccat ggctgactaa   8400
ttttttttat ttatgcagag gccgaggccg cctctgcctc tgagctattc cagaagtagt   8460
gaggaggctt ttttggaggc ctaggctttt gcaaaaagct cccgggagct gtatatcca   8520 ttttcggatc tgatcagcac gtgatgaaaa agcctgaact caccgcgacg tctgtcgaga   8580 agttctgat cgaaaagttc gacagcgtct ccgacctgat gcagctctcg gagggcgaag   8640
aatctcgtgc tttcagcttc gatgtaggag ggcgtggata tgtcctgcgg gtaaatagct   8700
gcgccgatgt ttctacaaa gatcgttatg tttatcggca cttttgcatcg gccgcgctcc   8760 cgattccgga agtgcttgac attggggaat tcagcgagag cctgacctat tgcatctccc   8820
gccgtgcaca gggtgtcacg ttgcaagacc tgcctgaaac cgaactgccc gctgttctgc   8880
agccggtcgc ggaggccatg gatgcgatcg ctgcggccga tcttagccag acgagcgggt   8940
tcggcccatt cggaccgcaa ggaatcggtc aatacactac atggcgtgat ttcatatgcg   9000
cgattgctga tccccatgtg tatcactggc aaactgtgat ggacgacacc gtcagtgcgt   9060
ccgtcgcgca ggctctcgat gagctgatgc tttgggccga ggactgcccc gaagtccggc   9120
```

-continued

```
acctcgtgca cgcggatttc ggctccaaca atgtcctgac ggacaatggc cgcataacag    9180
cggtcattga ctggagcgag gcgatgttcg gggattccca atacgaggtc gccaacatct    9240
tcttctggag gccgtggttg gcttgtatgg agcagcagac gcgctacttc gagcggaggc    9300
atccggagct tgcaggatcg ccgcggctcc gggcgtatat gctccgcatt ggtcttgacc    9360
aactctatca gagcttggtt gacggcaatt tcgatgatgc agcttgggcg cagggtcgat    9420
gcgacgcaat cgtccgatcc ggagccggga ctgtcgggcg tacacaaatc gcccgcagaa    9480
gcgcggccgt ctggaccgat ggctgtgtag aagtactcgc cgatagtgga aaccgacgcc    9540
ccagcactcg tccgagggca aaggaatagc acgtgctacg agatttcgat tccaccgccg    9600
ccttctatga aaggttgggc ttcggaatcg ttttccggga cgccggctgg atgatcctcc    9660
agcgcgggga tctcatgctg gagttcttcg cccacccccaa cttgtttatt gcagcttata    9720
atggttacaa ataaagcaat agcatcacaa atttcacaaa taaagcattt ttttcactgc    9780
attctagttg tggtttgtcc aaactcatca atgtatctta tcatgtctgt ataccgtcga    9840
cctctagcta gagcttggcg taatcatggt catagctgtt tcctgtgtga aattgttatc    9900
cgctcacaat tccacacaac atacgagccg gaagcataaa gtgtaaagcc tggggtgcct    9960
aatgagtgag ctaactcaca ttaattgcgt tgcgctcact gcccgctttc cagtcgggaa    10020
acctgtcgtg ccagctgcat taatgaatcg gccaacgcgc ggggagaggc ggtttgcgta    10080
ttgggcgctc ttccgcttcc tcgctcactg actcgctgcg ctcggtcgtt cggctgcggc    10140
gagcggtatc agctcactca aaggcggtaa tacggttatc cacagaatca ggggataacg    10200
caggaaagaa catgtgagca aaaggccagc aaaaggccag gaaccgtaaa aaggccgcgt    10260
tgctggcgtt tttccatagg ctccgccccc ctgacgagca tcacaaaaat cgacgctcaa    10320
gtcagaggtg gcgaaacccg acaggactat aaagatacca ggcgtttccc cctggaagct    10380
ccctcgtgcg ctctcctgtt ccgaccctgc cgcttaccgg atacctgtcc gcctttctcc    10440
cttcgggaag cgtggcgctt tctcatagct cacgctgtag gtatctcagt tcggtgtagg    10500
tcgttcgctc caagctgggc tgtgtgcacg aaccccccgt tcagcccgac cgctgcgcct    10560
tatccggtaa ctatcgtctt gagtccaacc cggtaagaca cgacttatcg ccactggcag    10620
cagccactgg taacaggatt agcagagcga ggtatgtagg cggtgctaca gagttcttga    10680
agtggtggcc taactacggc tacactagaa gaacagtatt tggtatctgc gctctgctga    10740
agccagttac cttcggaaaa agagttggta gctcttgatc cggcaaacaa accaccgctg    10800
gtagcggtgg tttttttgtt tgcaagcagc agattacgcg cagaaaaaaa ggatctcaag    10860
aagatccttt gatcttttct acggggtctg acgctcagtg gaacgaaaac tcacgttaag    10920
ggattttggt catgagatta tcaaaaagga tcttcaccta gatccttta aattaaaaat    10980 gaagttttaa atcaatctaa agtatatatg agtaaacttg gtctgacagt taccaatgct    11040
taatcagtga ggcacctatc tcagcgatct gtctatttcg ttcatccata gttgcctgac    11100
tccccgtcgt gtagataact acgatacggg agggcttacc atctggcccc agtgctgcaa    11160
tgataccgcg agacccacgc tcaccggctc cagatttatc agcaataaac cagccagccg    11220
gaagggccga gcgcagaagt ggtcctgcaa ctttatccgc ctccatccag tctattaatt    11280
gttgccggga agctagagta agtagttcgc cagttaatag tttgcgcaac gttgttgcca    11340
ttgctacagg catcgtggtg tcacgctcgt cgtttggtat ggcttcattc agctccggtt    11400
cccaacgatc aaggcgagtt acatgatccc ccatgttgtg caaaaaagcg gttagctcct    11460
tcggtcctcc gatcgttgtc agaagtaagt tggccgcagt gttatcactc atggttatgg    11520
```

```
cagcactgca taattctctt actgtcatgc catccgtaag atgctttct gtgactggtg    11580 agtactcaac caagtcattc tgagaatagt gtatgcggcg accgagttgc tcttgcccgg    11640
cgtcaatacg ggataatacc gcgccacata gcagaacttt aaaagtgctc atcattggaa    11700
aacgttcttc ggggcgaaaa ctctcaagga tcttaccgct gttgagatcc agttcgatgt    11760
aacccactcg tgcacccaac tgatcttcag catctttac tttcaccagc gtttctgggt    11820
gagcaaaaac aggaaggcaa aatgccgcaa aaaaggggat aagggcgaca cggaaatgtt    11880
gaatactcat actcttcctt tttcaatatt attgaagcat ttatcagggt tattgtctca    11940
tgagcggata catatttgaa tgtatttaga aaaataaaca aataggggtt ccgcgcacat    12000
ttccccgaaa agtgccacct gacgtcgacg gatcgggaga tcaacttgtt tattgcagct    12060
tataatggtt acaaataaag caatagcatc acaaatttca caaataaagc attttttttca    12120 ctgcattcta gttgtggttt gtccaaactc atcaatgtat cttatcatgt ctggatcaac    12180
tggataactc aagctaacca aaatcatccc aaacttccca ccccataccc tattaccact    12240
gccaattacc tgtggtttca tttactctaa acctgtgatt cctctgaatt attttcattt    12300
taaagaaatt gtatttgtta aatatgtact acaaacttag tagttggaag ggctaa        12356
```

```
<210> SEQ ID NO 16
<211> LENGTH: 12991
<212> TYPE: DNA
<213> ORGANISM: Artificial Sequence
<220> FEATURE:
<223> OTHER INFORMATION: plasmid = pXR002: EF1a-dCasRx-2A-EGFP (Addgene
      No. 109050)
<220> FEATURE:
<221> NAME/KEY: gene
<222> LOCATION: (2486)..(5383)
<223> OTHER INFORMATION: Codes for the RfxCas13d (dCasRx) protein

<400> SEQUENCE: 16
```

```
gctacagggc gcgtggggat acccccctaga gccccagctg gttctttccg cctcagaagc       60
catagagccc accgcatccc cagcatgcct gctattgtct tcccaatcct ccccccttgct      120 gtcctgcccc accccacccc ccagaataga atgacaccta ctcagacaat gcgatgcaat      180
ttcctcattt tattaggaaa ggacagtggg agtggcacct tccagggtca aggaaggcac      240
gggggagggg caaacaacag atggctggca actagaaggc acagtcgagg ctgatcagcg      300
ggtttaaacg ggccctgcta gagattttcc acactgacta aaagggtctg agggatctct      360
agttaccaga gtcacacaac agacgggcac acactacttg aagcactcaa ggcaagcttt      420
attgaggctt aagcagtggg ttccctagtt agccagagag ctcccaggct cagatctggt      480
ctaaccagag agacccagta cagtccggat gcagctctcg ggccatgtga tgaaatgcta      540
ggcggctgtc aaacctccac tctaatactt ctctctccgg gtcatccatc ccatgcaggc      600
tcacagggtg taacaagcgg gtgttctctc cttcattggc ttcttctacc ttctcttgct      660
caactggtac tagcttgtag caccatccaa aggtcagtgg atatctgatc cctggccctg      720
gtgtgtagtt ctgccaatca gggaagtagc cttgtgtgtg gtagatccac agatcaagga      780
tatcttgtct tcgttgggag tgaattagcc cttccagtcc cccctttct tttaaaaagt      840 ggctaagatc tacagctgcc ttgtaagtca ttggtcttaa aggtacctga ggtgtgactg      900
gaaaacccac ctcctcctcc tcttgtgctt ctagccaggc acaatcagca ttggtagctg      960
ctgtattgct acttgtgatt gctccatgtt tttctaggtc tcgaggtcga cggtatcgat     1020
gcggggaggc ggcccaaagg gagatccgac tcgtctgagg gcgaaggcga agacgcggaa     1080
```

```
gaggccgcag agccggcagc aggccgcggg aaggaaggtc cgctggattg agggccgaag      1140
ggacgtagca gaaggacgtc ccgcgcagaa tccaggtggc aacacaggcg agcagccaag      1200
gaaaggacga tgatttcccc gacaacacca cggaattgtc agtgcccaac agccgagccc      1260
ctgtccagca gcgggcaagg caggcggcga tgagttccgc cgtggcaata gggaggggga      1320
aagcgaaagt cccggaaagg agctgacagg tggtggcaat gccccaacca gtgggggttg      1380
cgtcagcaaa cacagtgcac accacgccac gttgcctgac aacgggccac aactcctcat      1440
aaagagacag caaccaggat ttatacaagg aggagaaaat gaaagccata cgggaagcaa      1500
tagcatgata caaaggcatt aaagcagcgt atccacatag cgtaaaagga gcaacatagt      1560
taagaatacc agtcaatctt tcacaaattt tgtaatccag aggttgatta tcgataagct      1620
tgatatcgaa ttcttacttg tacagctcgt ccatgccgag agtgatcccg gcggcggtca      1680
cgaactccag caggaccatg tgatcgcgct tctcgttggg gtctttgctc agggcggact      1740
gggtgctcag gtagtggttg tcgggcagca gcacggggcc gtcgccgatg ggggtgttct      1800
gctggtagtg gtcggcgagc tgcacgctgc cgtcctcgat gttgtggcgg atcttgaagt      1860
tcaccttgat gccgttcttc tgcttgtcgg ccatgatata gacgttgtgg ctgttgtagt      1920
tgtactccag cttgtgcccc aggatgttgc cgtcctcctt gaagtcgatg cccttcagct      1980
cgatgcggtt caccagggtg tcgccctcga acttcacctc ggcgcgggtc ttgtagttgc      2040
cgtcgtcctt gaagaagatg gtgcgctcct ggacgtagcc ttcgggcatg gcggacttga      2100
agaagtcgtg ctgcttcatg tggtcggggt agcggctgaa gcactgcacg ccgtaggtca      2160
gggtggtcac gagggtgggc cagggcacgg gcagcttgcc ggtggtgcag atgaacttca      2220
gggtcagctt gccgtaggtg gcatcgccct cgccctcgcc ggacacgctg aacttgtggc      2280
cgtttacgtc gccgtccagc tcgaccagga tgggcaccac cccggtgaac agctcctcgc      2340
ccttgctcac tgggccagga ttctcctcga cgtcaccgca tgttagcaga cttcctctgc      2400
cctctccact gccgctagca gcgtaatctg gaacatcgta tgggtaagcg gccgccacct      2460
tcctcttttt cttaggtccg gatccggaat tgccggacac cttcttttc tccttgtcga      2520 acttggcggc ctcgttccta tcgaacaggg cctcgatgct caggttctta aacctgggga      2580
tacagtagcc gaaaggcaca cacagcagtt tcaggagcct atcgttgtac ttcttctcgt      2640
cattcacagc gtcgaagtac tcggacacct ttccgctgct tttctcgtac ctctcattca      2700
tgataattct ctgcatgatg taatggtaca gttggaagta ggaattgacc tcggcaatgt      2760
cgttgatata ggcgtggaca tacctggcca cttccagggc gacggccttg tttgcgaaca      2820
gggtacatgt cttgttgtca attctcagga ggtcctccct gatgatcaca ttccacttgg      2880
tgttcctcag gtaggcgttc agggcggttt tggccttctc cctgttaatc tgcctggtga      2940
actcctcggc tttcttctcg tcgctgtatt tgatgtaatt ggcatacagc ttggggttgg      3000
cgctctcgag gctgtcaatg ctctccttgg ctctttcagc catctccttt ccacgtcct      3060 ttctcttatc gggggcagtt tcatcaatgc cagcgcagag cttggtgacg gagctgaatc      3120
ccttctcttc cagtttcttg agattgatgt cgtagccttt ctccttgtac agttgagcat      3180
cacgctcgac gcaatggaat ccgatgacgt acctggcgtt gatattgaca atattcttga      3240
ggatgtggta gatcacggtg aggtacaggc tgatgatctt tttaaacttc tccctctcgg      3300
cgttttccct gccggtgtcc tcaatgacgc tcctttcct gtcgaattgg tcgtagttca      3360
ttccggtgat gatctttgtg agagcgtcca cctttcgct cacgctcttg cccttatcct      3420
```

-continued

```
ttccgataca agtttcgtag tacctgtcga tctggttctt gccgttctgg ccctgttttt    3480
tctggatgtc agcgatcctg ccgagcacga acttcaccac ggcctcgttt ttggcgatct    3540
catggaggtg ggcaggatca ccgtatctga tcaggtagtg gaacctttta ttgctgatca    3600
cgttattaat aatgaaattt ctcatgccgt gcttgccttt cttgagcttg tttccgttct    3660
cgtccaggga aaaggtgtcg gcgagggcct tgagctcatc ataggacagg ttggttccta    3720
aaatacggat ggcgtcgata tacatggccc tcctggcatc ggcaataggt tctcccattc    3780
tagcgaagga cttgatcagc ctcagctcat cggcgatctt ggcggagtct ttgaaaaagg    3840
cgtattcctc cacgaactta gcgttgactc cgatgagagg catcaccttc aggaagctct    3900
ggatgttatc gaatttatta atcagggtgg tcaggaggtc gttgatctcc ttgccatcca    3960
ggaacatggt cagggcatac atgagtttgc tgaaggcgga aacatcacgg ccagcgggca    4020
ggattctggg cagtctaggg gcgtccttct tcttatactc tcttgtcttg tttcccctaa    4080
attccttgat gttgtgcatg atattttcga gctttctcca aattctatta gcttcatcgt    4140
agtagagggc atccttctgg tcgtcgttga aggagcccct caggttaatc acaaagatat    4200
ccttctcgct cagggacttc tcattatcgg ggagggactt attggcggca gccaccttgg    4260
catcctcttc gatgtaatac ctataaatca caaagtccat catggtgtag accttggtcc    4320
tgatggagtc gaacacctta tgattttcc tgatctcgga catatccttc ctgtccagca    4380
tcacttccct gagcttggtg atattgaatc cgaggttttt ctgctctttc ataatgctga    4440
atctgaaata ttgttcggcg aattcggcag ggttgattcc cagagtttcg gcaatatagt    4500
tcacgttggc ggcggagttc ttggagaagg agttggtcag ctcattggtg atcctgtcgt    4560
agaggtagtt gagggtggag atgtattcgt tgtcgaggtt cttatcgagg ttgtagagcc    4620
aggtcctgga gatcctggac tcttcttcgt tgttagcgac cacccagtgc gccagtccgc    4680
tcaggagggc cagaatgtca tagcattcgt tgccgtaatt gatgatgtaa tttctgccct    4740
ccttgctgaa aaaggcctgg ccgaaatagc cgagtctggg gttatcgagg aagttgtcga    4800
actcgtcata ctgggccttg atggcgttga tgagcttatc gttattgttg aaagcggccc    4860
tatggtgctc ggggtctttg aattcgtcgt aggtatacac tgtggagaac ttgccgaatc    4920
caataatgtc cttatccagg ccggagatat tgttgacggc gtaggcggcg ttggtaatgt    4980
attcggcgag gattttttca atgtccagga tgttatggat cacctggata caaatattgt    5040
cattgccatc agcgctctcg ccgaagtacc tcttttccag agtttccttc aggccgagca    5100
tatcctgctg gacgggtcct gtatacagag ggttgttagc caccacggcg tagcccttag    5160
gatggctgaa tttggcgttg ccgatcttat agccggcgtt tttatcggcc atttcagcgc    5220
tgaaggcctc gccctcattc acgctcctga tgctgtcgcc ctccacgatc ttttccagcc    5280
tggcgtcgct gccttcggcg aaggttgtca tgtacacttt ggagccggac acgagtgtgg    5340
acttcacgcc catgcccttg gcgaaggact ttttttttc gatgctggcc tccacctttc    5400
tcttcttctt ggggctcatg gtggccgtac gtcacgacac ctgaaatgga agaaaaaaac    5460
tttgaaccac tgtctgaggc ttgagaatga accaagatcc aaactcaaaa agggcaaatt    5520
ccaaggagaa ttacatcaag tgccaagctg gcctaacttc agtctccacc cactcagtgt    5580
ggggaaactc catcgcataa aacccctccc cccaacctaa agacgacgta ctccaaaagc    5640
tcgagaacta atcgaggtgc ctggacggcg cccggtactc cgtggagtca catgaagcga    5700
cggctgagga cggaaaggcc cttttccttt gtgtgggtga ctcacccgcc cgctctcccg    5760
agcgccgcgt cctccatttt gagctccctg cagcagggcc gggaagcggc catctttccg    5820
```

-continued

```
ctcacgcaac tggtgccgac cgggccagcc ttgccgccca gggcggggcg atacacggcg    5880
gcgcgaggcc aggcaccaga gcaggccggc cagcttgaga ctacccccgt ccgattctcg    5940
gtggccgcgc tcgcaggccc cgcctcgccg aacatgtgcg ctgggacgca cgggccccgt    6000
cgccgcccgc ggcccaaaa accgaaatac cagtgtgcag atcttggccc gcatttacaa    6060
gactatcttg ccagaaaaaa agcgtcgcag caggtcatca aaaattttaa atggctagag    6120
acttatcgaa agcagcgaga caggcgcgaa ggtgccacca gattcgcacg cggcggcccc    6180
agcgcccagg ccaggcctca actcaagcac gaggcgaagg ggctccttaa gcgcaaggcc    6240
tcgaactctc ccacccactt ccaacccgaa gctcgggatc aagaatcacg tactgcagcc    6300
aggtggaagt aattcaaggc acgcaagggc cataacccgt aaagaggcca ggcccgcggg    6360
aaccacacac ggcacttacc tgtgttctgg cggcaaaccc gttgcgaaaa agaacgttca    6420
cggcgactac tgcacttata tacggttctc ccccacccte gggaaaaagg cggagccagt    6480
acacgacatc actttcccag tttacccccgc gccaccttct ctaggcaccg gttcaattgc    6540
cgacccctcc ccccaacttc tcggggactg tgggcgatgt gcgctctgcc cactgacggg    6600
caccggagcc aattcccact cctttcaaga cctagaaggt ccattagctg caaagattcc    6660
tctctgttta aaactttatc catctttgca ttaattaacc aaactggatc tctgctgtcc    6720
ctgtaataaa cccgaaaatt ttgaattttt gtatttgtt tttgtaattc tttagtttgt    6780
atgtctgttg ctattatgtc tactattctt tccctgcac tgtaccccccc aatccccct    6840 tttctttaa aattgtggat gaatactgcc atttgtctgc agaattggcg cacgcagtgc    6900
cgatccgttc actaatcgaa tggatctgtc tctgtctctc tctccacctt cttcttctat    6960
tccttcgggc ctgtcgggtc ccctcggggt tgggaggtgg gtctgaaacg ataatggtga    7020
atatccctgc ctaactctat tcactataga aagtacagca aaaactattc ttaaacctac    7080
caagcctcct actatcatta tgaataattt tatataccac agccaatttg ttatgttaaa    7140
ccaattccac aaacttgccc atttatctaa ttccaataat tcttgttcat tcttttcttg    7200
ctggttttgc gattcttcaa ttaaggagtg tattaagctt gtgtaattgt taatttctct    7260
gtcccactcc atccaggtcg tgtgattcca aatctgttcc agagatttat tactccaact    7320
agcattccaa ggcacagcag tggtgcaaat gagtttttcca gagcaacccc aaatccccag    7380
gagctgttga tcctttaggt atctttccac agccaggatt cttgcctgga gctgcttgat    7440
gccccagact gtgagttgca acagatgctg ttgcgcctca atagccctca gcaaattgtt    7500
ctgctgctgc actataccag acaataattg tctggcctgt accgtcagcg tcattgacgc    7560
tgcgcccata gtgcttcctg ctgctcccaa gaacccaagg aacaaagctc ctattcccac    7620
tgctcttttt tctctctgca ccactcttct ctttgccttg gtgggtgcta ctcctaatgg    7680
ttcaattttt actactttat atttatataa ttcacttctc caattgtccc tcatatctcc    7740
tcctccaggt ctgaagatca gcggccgctt gctgtgcggt ggtcttactt ttgttttgct    7800
cttcctctat cttgtctaaa gcttccttgg tgtcttttat ctctatcctt tgatgcacac    7860
aatagagggt tgctactgta ttatataatg atctaagttc ttctgatcct gtctgaaggg    7920
atggttgtag ctgtcccagt atttgtctac agccttctga tgtttctaac aggccaggat    7980
taactgcgaa tcgttctagc tccctgcttg cccatactat atgtttttaat ttatattttt    8040 tctttccccc tggccttaac cgaatttttt cccatcgcga tctaattctc ccccgcttaa    8100
tactgacgct ctcgcaccca tctctctcct tctagcctcc gctagtcaaa attttttggcg    8160
```

-continued

```
tactcaccag tcgccgcccc tcgcctcttg ccgtgcgcgc ttcagcaagc cgagtcctgc     8220
gtcgagagag ctcctctggt ttccctttcg ctttcaagtc cctgttcggg cgccactgct     8280
agagattttc cacactgact aaaagggtct gagggatctc tagttaccag agtcacacaa     8340
cagacgggca cacactactt gaagcactca aggcaagctt tattgaggct taagcagtgg     8400
gttccctagt tagccagaga gctcccaggc tcagatctgg tctaaccaga gagacccagt     8460
acaggcaaaa cgcgctgctt atatagacct cccaccgtac acgcctaccg cccatttgcg     8520
tcaatggggc ggagttgtta cgacattttg gaaagtcccg ttgattttgg tgccaaaaca     8580
aactcccatt gacgtcaatg gggtggagac ttggaaatcc ccgtgagtca aaccgctatc     8640
cacgcccatt gatgtactgc caaaaccgca tcaccatggt aatagcgatg actaatacgt     8700
agatgtactg ccaagtagga aagtcccata aggtcatgta ctgggcataa tgccaggcgg     8760
gccatttacc gtcattgacg tcaatagggg gcgtacttgg catatgatac acttgatgta     8820
ctgccaagtg ggcagtttac cgtaaatact ccacccattg acgtcaatgg aaagtcccta     8880
ttggcgttac tatgggaaca tacgtcatta ttgacgtcaa tgggcggggg tcgttgggcg     8940
gtcagccagg cgggccattt accgtaagtt atgtaacgcg gaactccata tatgggctat     9000
gaactaatga ccccgtaatt gattactatt aataactagt caataatcaa tgtcaacgcg     9060
tatatctggc ccgtacatcg cgaagcagcg caaaacgcct aaccctaagc agattcttca     9120
tgcaattgtc ggtcaagcct tgccttgttg tagcttaaat tttgctcgcg cactactcag     9180
cgacctccaa cacacaagca gggagcagat actggcttaa ctatgcggca tcagagcaga     9240
ttgtactgag agtgcaccat aggggatcgg gagatctccc gatccgtcga cgtcaggtgg     9300
cacttttcgg ggaaatgtgc gcggaacccc tatttgttta tttttctaaa tacattcaaa     9360
tatgtatccg ctcatgagac aataaccctg ataaatgctt caataatatt gaaaaaggaa     9420
gagtatgagt attcaacatt tccgtgtcgc ccttattccc ttttttgcgg cattttgcct     9480
tcctgttttt gctcacccag aaacgctggt gaaagtaaaa gatgctgaag atcagttggg     9540
tgcacgagtg ggttacatcg aactggatct caacagcggt aagatccttg agagttttcg     9600
ccccgaagaa cgttttccaa tgatgagcac ttttaaagtt ctgctatgtg gcgcggtatt     9660
atcccgtatt gacgccgggc aagagcaact cggtcgccgc atacactatt ctcagaatga     9720
cttggttgag tactcaccag tcacagaaaa gcatcttacg gatggcatga cagtaagaga     9780
attatgcagt gctgccataa ccatgagtga taacactgcg gccaacttac ttctgacaac     9840
gatcggagga ccgaaggagc taaccgcttt tttgcacaac atgggggatc atgtaactcg     9900
ccttgatcgt tgggaaccgg agctgaatga agccatacca aacgacgagc gtgacaccac     9960
gatgcctgta gcaatggcaa caacgttgcg caaactatta actggcgaac tacttactct    10020
agcttcccgg caacaattaa tagactggat ggaggcggat aaagttgcag gaccacttct    10080
gcgctcggcc cttccggctg gctggtttat tgctgataaa tctggagccg gtgagcgtgg    10140
gtctcgcggt atcattgcag cactggggcc agatggtaag ccctcccgta tcgtagttat    10200
ctacacgacg gggagtcagg caactatgga tgaacgaaat agacagatcg ctgagatagg    10260
tgcctcactg attaagcatt ggtaactgtc agaccaagtt tactcatata ctttttagat    10320
tgatttaaaa cttcattttt aatttaaaag gatctaggtg aagatccttt ttgataatct    10380
catgaccaaa atcccttaac gtgagttttc gttccactga gcgtcagacc ccgtagaaaa    10440
gatcaaagga tcttcttgag atcctttttt tctgcgcgta atctgctgct tgcaaacaaa    10500
aaaaccaccg ctaccagcgg tggtttgttt gccggatcaa gagctaccaa ctctttttcc    10560
```

-continued

```
gaaggtaact ggcttcagca gagcgcagat accaaatact gttcttctag tgtagccgta   10620
gttaggccac cacttcaaga actctgtagc accgcctaca tacctcgctc tgctaatcct   10680
gttaccagtg gctgctgcca gtggcgataa gtcgtgtctt accgggttgg actcaagacg   10740
atagttaccg gataaggcgc agcggtcggg ctgaacgggg ggttcgtgca cacagcccag   10800
cttggagcga acgacctaca ccgaactgag atacctacag cgtgagctat gagaaagcgc   10860
cacgcttccc gaagggagaa aggcggacag gtatccggta agcggcaggg tcggaacagg   10920
agagcgcacg agggagcttc caggggggaaa cgcctggtat ctttatagtc ctgtcgggtt   10980
tcgccacctc tgacttgagc gtcgattttt gtgatgctcg tcaggggggc ggagcctatg   11040
gaaaaacgcc agcaacgcgg cctttttacg gttcctggcc ttttgctggc cttttgctca   11100
catgttcttt cctgcgttat cccctgattc tgtggataac cgtattaccg cctttgagtg   11160
agctgatacc gctcgccgca gccgaacgac cgagcgcagc gagtcagtga gcgaggaagc   11220
ggaagagcgc ccaatacgca aaccgcctct ccccgcgcgt tggccgattc attaatgcag   11280
ctggcacgac aggtttcccg actggaaagc gggcagtgag cgcaacgcaa ttaatgtgag   11340
ttagctcact cattaggcac cccaggcttt acactttatg cttccggctc gtatgttgtg   11400
tggaattgtg agcggataac aatttcacac aggaaacagc tatgaccatg attacgccaa   11460
gctctagcta gaggtcgacg gtatacgac atgataagat acattgatga gtttggacaa   11520
accacaacta gaatgcagtg aaaaaaatgc tttatttgtg aaatttgtga tgctattgct   11580
ttatttgtaa ccattataag ctgcaataaa caagttgggg tgggcgaaga actccagcat   11640
gagatccccg cgctggagga tcatccagcc ggcgtcccgg aaaacgattc cgaagcccaa   11700
cctttcatag aaggcggcgg tggaatcgaa atctcgtagc acgtgtcagt cctgctcctc   11760
ggccacgaag tgcacgcagt tgccggccgg gtcgcgcagg gcgaactccc gcccccacgg   11820
ctgctcgccg atctcggtca tggccggccc ggaggcgtcc cggaagttcg tggacacgac   11880
ctccgaccac tcggcgtaca gctcgtccag gccgcgcacc cacacccagg ccagggtgtt   11940
gtccggcacc acctggtcct ggaccgcgct gatgaacagg gtcacgtcgt cccggaccac   12000
accggcgaag tcgtcctcca cgaagtcccg ggagaacccg agccggtcgg tccagaactc   12060
gaccgctccg gcgacgtcgc gcgcggtgag caccggaacg gcactggtca acttggccat   12120
ggtttagttc ctcaccttgt cgtattatac tatgccgata tactatgccg atgattaatt   12180
gtcaacacgt gctgatcaga tccgaaaatg gatatacaag ctcccgggag cttttttgcaa   12240 aagcctaggc ctccaaaaaa gcctcctcac tacttctgga atagctcaga ggcagaggcg   12300
gcctcggcct ctgcataaat aaaaaaaatt agtcagccat ggggcggaga atgggcggaa   12360
ctgggcggag ttaggggcgg gatgggcgga gttaggggcg ggactatggt tgctgactaa   12420
ttgagatgca tgctttgcat acttctgcct gctggggagc ctggggactt ccacacctg   12480 gttgctgact aattgagatg catgctttgc atacttctgc ctgctgggga gcctggggac   12540
tttccacacc ctaactgaca cacattccac agaattaatt cgcgttaaat ttttgttaaa   12600
tcagctcatt ttttaaccaa taggccgaaa tcggcaaaat cccttataaa tcaaaagaat   12660
agaccgagat agggttgagt gttgttccag tttggaacaa gagtccacta ttaaagaacg   12720
tggactccaa cgtcaaaggg cgaaaaaccg tctatcaggg cgatggccca ctacgtgaac   12780
catcacccta atcaagtttt ttggggtcga ggtgccgtaa agcactaaat cggaaccta   12840 aagggagccc ccgatttaga gcttgacggg gaaagccggc gaacgtggcg agaaaggaag   12900
```

-continued

```
ggaagaaagc gaaaggagcg ggcgctaggg cgctggcaag tgtagcggtc acgctgcgcg    12960
taaccaccac acccgccgcg cttaatgcgc c                                   12991
```

```
<210> SEQ ID NO 17
<211> LENGTH: 780
<212> TYPE: DNA
<213> ORGANISM: Artificial Sequence
<220> FEATURE:
<223> OTHER INFORMATION: plasmid = BASU RaPID Plasma (Addgene No.
      107250) from Supplemental
<220> FEATURE:
<221> NAME/KEY: gene
<222> LOCATION: (1)..(780)
<223> OTHER INFORMATION: Codes for BASU protein

<400> SEQUENCE: 17
ggcaagttgt ctgaatcaga gattaggttt ggactgaaaa cggaggtgat gggccaacat      60
cttatctatc acgatgtttt gtccagcaca caaaagacag cccatgaatt ggcaaataac     120 aatgccccg agggtaccct cgtggttgca gataaacaga cagccggtag gggcgggatg      180
agccgagtgt ggcattctca agaaggaaac ggagtatgga tgagtttgat attgcgcccg     240
gacattccgc tccaaaagac gccccaactt accttgctgg cagctgtagc ggtggttcag     300
ggaatagaag aggccgcggg catacagact gatataaagt ggccgaacga catactcatt     360
aacgggaaaa aaacagtagg gatacttacc gaaatgcaag ctgaggagga tcgagtgcgc     420
tccgtgatta ttggtattgg cattaatgta aatcagcaac ccaatgattt ccccgatgag     480
ctcaaggaca ttgcgacgag tctgtcccag gcagctgggg aaaagatcga cagggcaggt     540
gtaatccagc atatcttgct ttgtttcgaa aagcgatacc gagactacat gacccacggt     600
ttcacgccca tcaagctctt gtgggagtca tacgccctcg gtattggcac gaacatgagg     660
gcgagaactc tcaacgggac attttacggt aaggcgttgg gtattgacga cgaaggggta     720
cttttgttgg aaactaatga aggcattaag aagatataca gcgcggacat cagccttagg     780
```

```
<210> SEQ ID NO 18
<211> LENGTH: 2897
<212> TYPE: DNA
<213> ORGANISM: Artificial sequence
<220> FEATURE:
<223> OTHER INFORMATION: Sequence for the dCasRx protein
<220> FEATURE:
<221> NAME/KEY: gene
<222> LOCATION: (1)..(2897)
<223> OTHER INFORMATION: The reverse strand sequence codes for the
      RfxCas13d (dCasRx) protein

<400> SEQUENCE: 18
atcgaaaaaa aaaagtcctt cgccaagggc atgggcgtga agtccacact cgtgtccggc      60
tccaaagtgt acatgacaac cttcgccgaa ggcagcgacg ccaggctgga aaagatcgtg     120
gagggcgaca gcatcaggag cgtgaatgag ggcgaggcct tcagcgctga aatggccgat     180
aaaaacgccg gctataagat cggcaacgcc aaattcagcc atcctaaggg ctacgccgtg     240
gtggctaaca accctctgta tacaggaccc gtccagcagg atatgctcgg cctgaaggaa     300
actctggaaa agaggtactt cggcgagagc gctgatggca atgacaatat ttgtatccag     360
gtgatccata acatcctgga cattgaaaaa atcctcgccg aatacattac caacgccgcc     420
tacgccgtca caatatctc cggcctggat aaggacatta ttggattcgg caagttctcc     480
acagtgtata cctacgacga attcaaagac cccgagcacc ataggccgc tttcaacaat     540 aacgataagc tcatcaacgc catcaaggcc cagtatgacg agttcgacaa cttcctcgat     600
```

```
aaccccagac tcggctattt cggccaggcc tttttcagca aggagggcag aaattacatc    660
atcaattacg gcaacgaatg ctatgacatt ctggccctcc tgagcggact ggcgcactgg    720
gtggtcgcta acaacgaaga agagtccagg atctccagga cctggctcta caacctcgat    780
aagaacctcg acaacgaata catctccacc ctcaactacc tctacgacag gatcaccaat    840
gagctgacca actccttctc caagaactcc gccgccaacg tgaactatat tgccgaaact    900
ctgggaatca accctgccga attcgccgaa caatatttca gattcagcat tatgaaagag    960
cagaaaaacc tcggattcaa tatcaccaag ctcagggaag tgatgctgga caggaaggat    1020
atgtccgaga tcaggaaaaa tcataaggtg ttcgactcca tcaggaccaa ggtctacacc    1080
atgatggact ttgtgattta taggtattac atcgaagagg atgccaaggt ggctgccgcc    1140
aataagtccc tccccgataa tgagaagtcc ctgagcgaga aggatatctt tgtgattaac    1200 ctgagggget ccttcaacga cgaccagaag gatgccctct actacgatga agctaataga    1260
atttggagaa agctcgaaaa tatcatgcac aacatcaagg aatttagggg aaacaagaca    1320
agagagtata agaagaagga cgcccctaga ctgcccagaa tcctgccccgc tggccgtgat    1380 gtttccgcct tcagcaaact catgtatgcc ctgaccatgt tcctggatgg caaggagatc    1440
aacgacctcc tgaccaccct gattaataaa ttcgataaca tccagagctt cctgaaggtg    1500
atgcctctca tcggagtcaa cgctaagttc gtggaggaat acgccttttt caaagactcc    1560
gccaagatcg ccgatgagct gaggctgatc aagtccttcg ctagaatggg agaacctatt    1620
gccgatgcca ggagggccat gtatatcgac gccatccgta tttttaggaac caacctgtcc    1680 tatgatgagc tcaaggccct cgccgacacc ttttccctgg acgagaacgg aaacaagctc    1740
aagaaaggca agcacggcat gagaaatttc attattaata acgtgatcag caataaaagg    1800
ttccactacc tgatcagata cggtgatcct gcccacctcc atgagatcgc caaaaacgag    1860
gccgtggtga agttcgtgct cggcaggatc gctgacatcc agaaaaaaca gggccagaac    1920
ggcaagaacc agatcgacag gtactacgaa acttgtatcg gaaaggataa gggcaagagc    1980
gtgagcgaaa aggtggacgc tctcacaaag atcatcaccg gaatgaacta cgaccaattc    2040
gacaagaaaa ggagcgtcat tgaggacacc ggcagggaaa acgccgagag ggagaagttt    2100
aaaaagatca tcagcctgta cctcaccgtg atctaccaca tcctcaagaa tattgtcaat    2160
atcaacgcca ggtacgtcat cggattccat tgcgtcgagc gtgatgctca actgtacaag    2220
gagaaaggct acgacatcaa tctcaagaaa ctggaagaga agggattcag ctccgtcacc    2280
aagctctgcg ctggcattga tgaaactgcc cccgataaga gaaaggacgt ggaaaaggag    2340
atggctgaaa gagccaagga gagcattgac agcctcgaga gcgccaaccc caagctgtat    2400
gccaattaca tcaaatacag cgacgagaag aaagccgagg agttcaccag gcagattaac    2460
agggagaagg ccaaaaccgc cctgaacgcc tacctgagga caccaagtg gaatgtgatc    2520 atcagggagg acctcctgag aattgacaac aagacatgta ccctgttcgc aaacaaggcc    2580
gtcgccctgg aagtggccag gtatgtccac gcctatatca cgacattgc cgaggtcaat    2640 tcctacttcc aactgtacca ttacatcatg cagagaatta tcatgaatga gaggtacgag    2700
aaaagcagcg gaaaggtgtc cgagtacttc gacgctgtga atgacgagaa gaagtacaac    2760
gataggctcc tgaaactgct gtgtgtgcct ttcggctact gtatccccag gtttaagaac    2820
ctgagcatcg aggccctgtt cgataggaac gaggccgcca agttcgacaa ggagaaaaag    2880
aaggtgtccg gcaattc                                                   2897
```

METHOD FOR DETERMINING LONG NON-CODING RIBONUCLEIC ACID INTERACTION PROTEINS

SEQUENCE LISTING

The Sequence Listing file entitled "sequencelisting" having a size of 2,704 bytes and a creation date of Apr. 26, 2021, that was filed with the patent application is incorporated herein by reference in its entirety.

TECHNICAL FIELD

The present invention relates to a novel method for determining long non-coding ribonucleic acid interaction proteins.

BACKGROUND ART

Although only 2% sequences of the human genome code protein, more than 70% of genomic DNA can be transcribed into RNA at different stages of development. For decades, these huge numbers of non-coding RNAs (ncRNAs) have been considered as "dark matter" and their functions remained to be developed. These ncRNAs, especially long non-coding ribonucleic acids (lncRNA, defined as ncRNAs with more than 200 nucleotides in length) have been of interest recently, which were generally considered to be an important part participating in epigenetic regulation. For example, various lncRNAs were involved in cell cycle regulation and proliferation, the dysregulation of which is associated with progression and metastasis of various cancers.

XIST (X-inactivation specific transcript) is one of the first widely studied lncRNAs, which directs X chromosome inactivation (XCI) in female mammals, thus balancing the dose of genes between XY males and XX females. Its ability to constrain chromatin binding proteins makes it possible to label allele and cis-regulate transcription. At present, XCI and XIST have become exemplary models for understanding the epigenetic regulation of lncRNA.

The interaction between lncRNA and RNA binding proteins (RBP) determines the function and fate of RNA molecules. Up to 8.5 percent of the entire human proteome was predicted to have RNA binding properties, further demonstrating the multiple functions of lncRNA in various biological events. Mutations in lncRNA transcripts or changes in the abundance of lncRNA may alter their associated proteome, leading to health problems. The identification of lncRNA-related proteins will reveal the molecular mechanisms of the cell function in complex human diseases.

Although there is a growing recognition of the functional importance of RBP, there are significant technical limitations in elucidating lncRNA-protein interactions in living cells at present. Current methods depend mainly on chemical or UV mediated cross-linking between RNA and protein molecules to achieve effective enrichment and separation for the complex. Such procedures may produce non-systematic biases in physiological situations and mask the interaction proteins.

Recently, Ramanathan, M. et al. developed a RaPID method that integrates the promiscuous but efficient biotin ligase BASU with a AN peptide navigation system that recognizes the stem-loop of RNA BoxB. Compared with other biotin ligase variants, BASU remains inactive until it is rapidly activated by the high concentration of exogenous biotin in the culture medium, thereby labeling proteins nearby in a smaller labeling radius (~10 nm) in a shorter reaction time. This feature greatly reduces non-specific background noise. However, the target RNA needs to be artificially fused with the BoxB stem-loop close to the RBP binding region, and it needs to be expressed ectopically in the cell. Therefore, RaPID must compromise on three important factors: firstly, the abundance of ectopically expressed target RNA greatly exceeds the endogenous level of the transcript, resulting in a non-physiological balance of the interaction between RNA and RBP; secondly, the incorporation of the hairpin structure BoxB into the target RNA may interfere with the natural structure of the transcript, thereby changing its binding protein; thirdly, BASU can only label the RBP adjacent to the stem loop of BoxB at the 5' or 3' end of the RNA, therefore, some important RBPs may be missed, especially for long transcripts such as XIST (~19 kb). Briefly, the potential shortcomings, including the loss of cellular background, extensive molecular engineering and possible destruction of the natural structure of RNA, greatly limit the wide application of this method.

SUMMARY OF INVENTION

An object of the present invention is to provide a novel method for determining long non-coding ribonucleic acid (lncRNA) interaction proteins.

The present invention provides a CRISPR-Assisted RNA-Protein Interaction Detection (CARPID) method, which integrates CRISPR/CasRx based RNA targeting and proximity markers to identify binding proteins of specific lncRNAs within cells at natural state.

The inventive technology for detecting CRISPR-assisted RNA-protein interaction can be used as a novel and powerful method to find the interaction proteins of lncRNA in living cells. The method uses the highly specific CRISPR/CasRx system fused to the promiscuous but efficient biotin ligase BASU. The interaction with various proteins plays a central role in the regulatory activity of lncRNA. The present invention relates to a fusion protein of BASU and dCasRx, which comprises the dCasRx of compact Type VI-D CRISPR single-effect system, which can find the target lncRNA by specific gRNA co-transfected into the target cell. Once binding to the target lncRNA, it can enable BASU to specifically biotinylate effector proteins nearby activated by a high concentration of biotin. The biotinylated protein is separated by streptavidin affinity-coupled magnetic beads, then eluted, trypsin-digested and quantitatively analyzed by label-free mass spectrometry. As a control group, cells transfected with BASU-dCasRx but without gRNA are used as background.

At the time of the results analysis, the proteins identified in the specific gRNA group are statistically compared with the control group (no gRNA) for enrichment or reduction. Rank product is a non-parametric statistical method used to calculate the false discovery rate (FDR) of enrichment. In order to generate a list of specific interaction proteins, the critical value is set as enrichment≥2 times and FDR≤0.05. The obtained protein can be used for gene ontology analysis or protein interaction network analysis. In addition, a comprehensive analysis is performed on the target protein by using gRNA targeting different regions, thereby obtaining a high-resolution spectrum of the target lncRNA interaction protein.

In an aspect, the present invention thus provides a fusion protein formed by BASU and dCasRx.

According to the embodiment of the present invention, the fusion protein can be BASU-dCasRx, or dCasRx-BASU.

In another aspect, the invention further provides an expression vector for expressing the fusion protein formed by BASU and dCasRx. Preferably, it is a mammalian expression vector.

In another aspect, the invention further provides a composition comprising: the fusion protein formed by BASU and dCasRx and/or the expression vector for expressing the fusion protein formed by BASU and dCasRx, as well as a gRNA targeting the target lncRNA.

In another aspect, the invention further provides a kit for determining lncRNA interaction proteins, comprising: the fusion protein formed by BASU and dCasRx and/or the expression vector for expressing the fusion protein formed by BASU and dCasRx, as well as a gRNA targeting the target lncRNA. Preferably, the kit further comprises a control reagent without gRNA (for example, co-transfected with the gRNA empty vector and the BASU-dCasRx fusion protein expression vector).

In another aspect, the present invention further provides a method for determining lncRNA interaction proteins, comprising:

co-transfecting the expression vector for expressing the fusion protein formed by BASU and dCasRx, and a gRNA that specifically targets the target lncRNA in a target cell, thereby BASU specifically biotin-labeling effector proteins nearby;

isolating the biotinylated proteins for analysis to determine the lncRNA interaction proteins.

According to a specific embodiment of the present invention, in the method for determining lncRNA-interaction proteins of the present invention, specifically, the biotinylated protein can be separated by streptavidin affinity-coupled magnetic beads, and then eluted and trypsin digested, and quantitatively analyzed by a label-free mass spectrometry.

According to a specific embodiment of the present invention, the method for determining the lncRNA interaction protein of the present invention is used to determine the lncRNA interaction protein in living cells.

According to a specific embodiment of the present invention, the method for determining lncRNA-interaction proteins of the present invention further comprises: statistically comparing the protein identified in the specific gRNA group with the control group without gRNA for enrichment or reduction.

According to a specific embodiment of the present invention, the method for determining a lncRNA-interaction protein of the present invention further comprises: calculating the false discovery rate of enrichment by Rank product; more preferably, the critical value is set as enrichment≥2 times and FDR≤0.05.

According to a specific embodiment of the present invention, the method for determining a lncRNA-interaction protein of the present invention further comprises:

performing a genetic ontological analysis or protein interaction network analysis on the obtained proteins; and/or performing a comprehensive analysis on the target protein by using gRNA targeting different regions to obtain a high-resolution spectrum of the target lncRNA interaction protein.

In another aspect, the invention further provides a method for analyzing enriched interaction proteins to specific regions of target lncRNA, comprising:

performing an enrichment analysis on the proteins with more than one peptide fragments detected; wherein the proteins preferably comprise human keratin;

normalizing and logarithmizing a LFQ abundance of each group;

replacing a missing value by a minimum value representing the detection limit of mass spectrometer;

determining the protein that is statistically enriched in samples of the gRNA transfection group compared to the control group transfected with gRNA empty vectors by rank product;

a protein with the adjusted p-value≤0.05 and the abundance change≥2 folds, is identified as RBP to the target lncRNA.

In another aspect, the present invention further provides a proteomics method for defining a high-resolution spectrum of the interaction protein for the target lncRNA. By applying specific gRNA to different regions of the target lncRNA, the interaction protein of the specific region can be obtained.

In another aspect, the present invention also provides an analysis system (device) for determining lncRNA interaction proteins, which includes a data analysis unit configured to enrich and analyze the protein with more than one peptide detected by the present invention, and further analyze to determine the lncRNA interaction protein. Specifically, the protein with more than one peptide includes human keratin. The specific analysis process comprises: normalizing and logarithmizing a LFQ abundance of each group; replacing a missing value by a minimum value representing the detection limits of mass spectrometer; determining the protein that is statistically enriched in samples of the gRNA transfection group compared to the control group transfected with gRNA empty vectors by rank product; a protein with the adjusted p-value≤0.05 and the abundance change≥2 folds, is identified as RBP to the target lncRNA.

In some specific embodiments of the present invention, CARPID is applied to three lncRNAs, namely XIST, DANCR and MALAT1, in the present invention, and reliably recognizes their known interaction proteins. It is worth noting that these three groups of interaction proteins have almost no overlap, showing the strong specificity of the method of the present invention.

In some specific embodiments of the present invention, the CARPID technology of the CRISPR auxiliary system of the present invention systematically detects the lncRNA XIST binding protein group in a non-crosslinking manner. Using CARPID, the present invention not only detects a number of previously reported XIST binding proteins, but also identifies many new factors, among which the present invention validates the TAF15 and SNF2L in this study through biochemical and functional verification. The data of the present invention supports the current consensus that XIST RNA regulates XCI by recruiting chromatin remodeling agents for chromosome condensation and isolating transcription mechanisms to further inhibit genes.

In order to maximize the credibility of the present invention and avoid false positive signals, the present invention controls the changes at both the experimental and statistical levels. Firstly, a self-cleavable GFP fusion is used to monitor the expression of BASU enzyme in cells and minimize the reaction time required for effective biotin labeling. Secondly, a multi-site targeting strategy is adopted to specifically target three different loci on XIST, and new proteins identified with at least two gRNA pairs are further verified in the present invention. Thirdly, for each group of gRNA, at least three repeated CARPID experiments are repeated. In addition, a triple simulation control is used to evaluate the statistical significance of the enrichment.

The present invention also proves that CARPID can be universally used to detect the bound proteome of lncRNA.

The present invention specifically targets the other two lncRNA DANCR and MALAT1 with different length expression levels and subcellular localization. The dysregulations of DANCR and MALAT1 expression relate to a variety of malignant tumors, including liver cancer, breast cancer, glioma, colorectal cancer, gastric cancer and lung cancer. The research of the present invention shows that DANCR can interact with proteins largely enriched in extracellular exosomes. Interestingly, it has been reported in various studies that serum DANCR levels are elevated in cancer patients. In addition, the present invention also identifies the interaction between DANCR and Ezrin (an important structural protein in the cell cortex). Such findings reveal the new function of lncRNA in tumor development.

Label-free mass spectrometry is a direct and cost-effective method to apply CARPID. In addition, it has low technical requirements, thus ensuring wide applicability. The present invention has shown that CARPID is a powerful method for detecting RNA binding proteins, with high specificity and reproducibility. To further improve the resolution, quantitative mass spectrometry with different labeling strategies (such as TMT and other isobaric chemical labeling and SILAC labeling) can be incorporated into the CARPID channel.

In summary, the present invention combines CARPID, labeled quantitative mass spectrometry and non-parametric enrichment analysis, and can identify specific lncRNA interaction proteins in living cells with high confidence by using proteomics methods. The CARPID technology of the present invention can draw a high-resolution spectrum of various lncRNAs interaction proteins involved in human diseases. Such spectrum can provide guidance for therapies that interfere with the function of specific lncRNAs.

DESCRIPTION OF DRAWINGS

The patent or application file contains at least one drawing executed in color. Copies of this patent or patent application publication with color drawing(s) will be provided by the Office upon request and payment of the necessary fee.

FIGS. 1a to 1e show that CARPID is used to identify proteins associated with lncRNA XIST in living cells, wherein:

FIG. 1a is a schematic diagram of CARPID workflow. The target lncRNA is targeted by a group of gRNAs. The nuclease activity-free RNA nuclease CRISPR/CasRx (dCasRx) fused with engineered biotin ligase (BASU) is recruited to a specific site. After a treatment by biotin, the adjacent RNA binding protein (RBP) will be biotinylated by BASU. The red shading indicates the marking radius of BASU-dCasRx. Biotinylated proteins are enriched by streptavidin affinity-coupled magnetic beads (MyOne T1) for subsequent mass spectrometry (MS) identification and Western blot (WB) analysis.

FIG. 1b shows three groups of gRNAs (highlighted in different colors) against the human lncRNA XIST locus. Only one group of gRNA is expressed in each experiment.

FIG. 1c shows that CARPID is used to identify XIST-related proteomes. The volcano plot shows the enrichment of XIST-related proteins in HEK293T cells. The x-axis represents the log 2 converted value of the protein level fold change in the CARPID results of all three groups of XIST gRNAs compared with the control. The y-axis shows the negative logarithmic converted p-value (non-parametric rank product test). Significantly enriched proteins are marked as orange dots. Proteins previously verified to interact with XIST and recognized by CARPID are marked in orange font. The blue font represents SNF2L and TAF15, which are two newly identified XIST-related proteins.

FIG. 1d shows the XIST-protein interaction network identified by CARPID. White nodes indicate proteins recognized only in a group of gRNAs. The pink nodes represent the proteins recognized in two groups of gRNA. The red nodes show the proteins recognized in all three groups of gRNA. A line is connected between two proteins evaluated as interaction (STRING interaction score≥0.40). The width of the line is proportional to the STRING interaction score. The nodes with purple edges highlight the proteins involved in chromatin remodeling. XIST-related proteins are highlighted in bold orange (19 proteins). The blue font represents SNF2L and TAF15, which are two newly identified XIST-related proteins.

FIG. 1e shows the top five important gene ontology (GO) semantics of XIST-related proteins.

FIGS. 2a to 2h show the analysis results that verify the proteins associated with XIST, wherein:

FIG. 2a shows the verification of the XIST-TAF15 interaction using WB and immunoFISH. The upper panel shows that Western blotting is performed using anti-human TAF15 antibody after CARPID. From the lysate of HEK293T cells co-transfected with BASU-dCasRx and each of pre-gRNA (control), and the gRNAs specifically targeting locus 1 (XIST-L1), locus 2 (XIST-L2) and locus 3 (XIST-L3), the biotinylated protein is precipitated using streptavidin affinity-coupled magnetic beads. The experiment is carried out in three biological replicates and showed representative results. The lower panel shows the immunoFISH test results of TAF15 and XIST. HEK293T cells are fixed and incubated with anti-TAF15 antibody and corresponding secondary antibody with CF 488A (green). A specific oligonucleotide probe labeled as Cy3 (red) is used to detect XIST. The nucleus is counterstained with DAPI (blue). The box area in the left image is enlarged and displayed on the right. The scale is shown. This image is representative of three independent biological experiments.

FIG. 2b shows the TAF15 CLIP-seq data result of mouse brain tissue displayed by the genome browser view. This figure shows that TAF15 specifically binds to XIST RNA. The non-redundant readings of the two chains are displayed separately. The RefSeq gene also indicates chain information in different colors: red, forward strand; blue, reverse strand.

FIG. 2c shows a histogram showing the number of TAF15 binding peaks on the XIST transcript compared to the expected peak number (mean±SD) based on 10,000 random shuffle peak positions. The peak sites are directly extracted from the article by Kapeli et al. The p-value is based on the one-tailed Poisson test.

FIG. 2d shows TAF15 antibody is used in HEK293T cells with IgG as a control, and formaldehyde-assisted RIP is used to verify the XIST-TAF15 interaction. Quantitative enrichment is performed using RT-qPCR in three different regions of XIST and two different regions of MALAT1. GAPDH served as an internal control. Data is expressed as mean±SD, n=3; ** indicates p<0.01 using the unpaired Student's t test. The upper right figure shows the results of TAF15 antibody and IgG immunoprecipitation experiments.

FIG. 2e shows HTR-SELEX is used to verify the XIST-TAF15 interaction. The blue curve shows the predicted binding affinity of TAF15 along the XIST transcript. The x-axis represents the relative position of the human XIST transcript (~19 kb). The y-axis shows the gkm-SVM scores of 7 monomers starting from the corresponding position in XIST. Please note that the larger the gkm-SVM score, the higher the affinity of TAF15. The three colored vertical lines represent locus 1-3 of XIST. The blue curve shows the fitted value of the generalized additive model, while the gray area shows a confidence interval of 95%. As a genomic background, the orange curve shows the average gkm-SVM score of 1,000 sequences randomly sampled from the human genome (hg19).

FIG. 2f shows the verification of the XIST-SNF2L interaction using WB and immunoFISH. The upper panel shows that Western blotting is performed using anti-human SNF2L antibody after CARPID. From the lysate of HEK293T cells co-transfected with BASU-dCasRx and each of pre-gRNA (control), and the gRNAs specifically targeting locus 1 (XIST-L1), locus 2 (XIST-L2) and locus 3 (XIST-L3), the biotinylated protein is precipitated using streptavidin affinity-coupled magnetic beads. The experiment is carried out in three biological replicates and showed representative results. The lower panel shows the immunoFISH test results of SNF2L and XIST. HEK293T cells are fixed and incubated successively with anti-TAF15 antibody and corresponding secondary antibody with CF 488A (green). A specific oligonucleotide probe labeled as Cy3 (red) is used to detect XIST. The nucleus is counterstained with DAPI (blue). The box area in the left image is enlarged and displayed on the right. The experiment is performed in three biological replicates and showed representative results.

FIG. 2g shows SNF2L antibody is used in HEK293T cells with IgG as a control, and formaldehyde-assisted RIP is used to verify the XIST-TAF15 interaction. Quantitative enrichment is performed using RT-qPCR in three different regions of XIST and two different regions of MALAT1. GAPDH served as an internal control. Data is expressed as mean±SD, n=3; ** indicates p<0.01 using the unpaired Student's t test. The upper right figure shows the results of SNF2L antibody and IgG immunoprecipitation experiments.

FIG. 2h shows the effects of TAF15 and SNF2L in X-linked inhibition in mice. Female iMEF cells (E2C4) contain the GFP transgene on the inactivated X chromosome, and its expression is completely suppressed (NT). After 5-aza treatment (NT+5-aza), GFP is derepressed. Various shRNAs are used to knock out SmcHD1, TAF15 and SNF2L, and the GFP expression level is determined by RT-qPCR. Data is expressed as mean±SD, n=3, *p<0.05, **p<0.01, Student's t test.

FIGS. 3a to 3e show the identification of lncRNA DANCR and MALAT1 related proteins by CARPID in living cells, wherein:

FIG. 3a shows the identification of the DANCR-related proteome associated with CARPID. The volcano plot shows the enrichment of DANCR-related proteins in HEK293T cells. The x-axis represents the log 2 conversion of the protein level fold change in the CARPID combined with the two groups of DANCR gRNA in comparison with the control. The y-axis shows the negative logarithmic converted p-value (non-parametric rank product test). Significantly enriched proteins are marked as orange dots.

FIG. 3b shows the DANCR-protein interaction network identified by CARPID. White nodes indicate proteins recognized only in a group of gRNAs. The pink nodes represent the proteins recognized in two groups of gRNAs. A line is connected between two proteins evaluated as interaction (STRING interaction score≥0.40). The width of the line is proportional to the STRING interaction score.

FIG. 3c shows the proteome associated with MALAT1 identified by CARPID. The volcano plot shows the enrichment of MALAT1 related proteins in HEK293T cells. The x-axis represents the log 2 conversion of the protein level fold change in the CARPID combined with the two groups of MALAT1 gRNA in compared with the control. The y-axis shows the negative logarithmic converted p-value (non-parametric rank product test). Significantly enriched proteins are marked with orange dots.

FIG. 3d shows the MALAT1 protein interaction network identified by CARPID. White nodes indicate proteins recognized in a group of gRNAs. The pink nodes represent proteins recognized in two groups of gRNAs. A line is connected between two proteins evaluated as interaction (STRING interaction score≥0.40). The width of the line is proportional to the STRING interaction score.

FIG. 3e shows the comparison of CARPID results between different lncRNAs. The Venn diagram illustrates the unique and specific RBP between each two of the three lncRNAs (XIST, DANCR, and MALAT1).

FIGS. 4a to 4e are the optimized schematic diagrams of CARPID, wherein:

FIG. 4a shows the position of the three groups of gRNA on XIST. Different colors indicate different gRNA groups. Note that the interval between the two individual gRNAs in each group is approximately 15 nt.

FIG. 4b shows the scheme of the BASU-dCasRx construct. BASU is subcloned from BASU RaPID plasmid (Addgene #107250), which has the nucleotide sequence of SEQ. ID NO 15 and/or SEQ. ID NO 17, and cloned into EF1a-dCasRx-2A-EGFP plasmid (Addgene #109050), which has the nucleotide sequence of SEQ. ID NO 16. SEQ ID NO 18 is a reverse strand segment of the sequence of SEQ ID NO 16.

FIG. 4c shows the transfection of HEK293T cells with BASU-dCasRx or dCasRx-BASU. After 48 hours, the cells are treated with 200 μM biotin for the specified time. Immunoblotting experiments are performed on whole cell lysates using streptavidin chelating HRP. The experiment is carried out in 3 biological replicates, and representative results are shown).

FIG. 4d is a scatter plot showing the comparison of gene expression levels in wild-type HEK293T cells or HEK293T cells transfected with different gRNAs (XIST-L1/XIST-L2/XIST-L3). The x-axis in each figure represents the log 2 converted gene expression level in wild-type HEK293T cells. The y-axis represents the log 2 converted gene expression level of HEK293T cells transfected with gRNA in the CARPID experiment. Each figure indicates the expression level of XIST gene.

FIG. 4e shows the specificity of the CRISPR/CasRx system on XIST. HEK293T cells are co-transfected with CasRx and single gRNA (empty vector control, XIST-L1, XIST-L2 and XIST-L3). Total RNA is extracted from the treated cells and then subjected to reverse transcription and qPCR analysis to quantify the level of XIST specific sites. GADPH is used to normalize the level of XIST. Please note that the co-transfection with CasRx and gRNA specifically reduces the RNA transcription level at its target locus. Data is expressed as mean±SD, n=3, *** p<0.001, unpaired Student's t-test.

FIG. 5 shows the secondary structure location mapping of XIST gRNA. The XIST-L1/L2/L3 genome browser view on XIST hairpin structure information by Lu et al. uses black strings to represent regions with complementary pairs. The vertical lines in different colors highlight the location of the different gRNA groups of the targeted locus on the XIST lncRNA. The locations of known domains (A-H) are also indicated.

FIGS. 6a to 6c show the CARPID results of XIST, wherein:

FIG. 6a shows the use of the Venn diagram to illustrate the overlap/repeatability of the CARPID mass spectrometry identification results of three different XIST gRNAs (XIST-L1/XIST-L2/XIST-L3).

FIG. 6b shows the use of the Venn diagram to illustrate the overlap of the proteins significantly enriched in the CARPID mass spectrometry identification results of three different groups of XIST gRNA (XIST-L1/XIST-L2/XIST-L3).

FIG. 6c shows the identification of XIST binding proteins using CARPID. The volcano plot shows the enrichment of XIST-related proteins in HEK293T cells. The x-axis represents the log 2 converted value of the protein level fold change in the CARPID results of all three groups of XIST gRNAs compared with the control. The y-axis shows the negative logarithmic converted p-value (non-parametric rank product test). Significantly enriched proteins are marked with orange dots. Proteins previously known to interact with XIST and recognized by CARPID are marked in orange font. The blue font represents SNF2L and TAF15, which are two newly identified XIST-related proteins.

FIG. 7 shows the quantitative analysis of CARPID-WB. The results of CARPID are tested by western blotting, using TAF15 and SNF2L antibodies. The streptavidin affinity-coupled magnetic beads are added to lysate of the HEK293T cell transfected with BASU-dCasRx, as well as pre-gRNA (control), locus 1 (XIST-L1), locus 2 (XIST-L2) or locus 3 (XIST-L3), to precipitate the biotinylated protein. The experiment is carried out in three biological replicates and representative results are shown. The WB signal is quantified using ImageJ software (version 1.8.0_172).

FIGS. 8a to 8d show TAF15 HTR-SELEX, wherein:

FIG. 8a shows the design scheme for the oligonucleotide of HTR-SELEX. These oligonucleotides contain T7 promoter, Illumina adaptor (P5/P7) and 40-nt random sequence.

FIG. 8b is a schematic diagram of the HTR-SELEX experiment. First, the synthesized DNA template library is transcribed into RNA, and TAF15 protein is expressed in *Escherichia coli* Rosetta P3 DE LysS strain. After bound, washed and eluted, the remaining (bound) RNA is subjected to reverse transcription and PCR amplification to obtain an NGS sequencing library. The DNA library is sequenced by the Illumina Hiseq 4000 for molecular counting, and part of the library is used as input for the next round of HTR-SELEX (see methods for details).

FIG. 8c shows the RNA binding motif of TAF15 enriched from the HTR-SELEX analysis.

FIG. 8d shows the machine learning scheme. A machine learning algorithm (gkm-SVM) based on gap k-mer is adopted in the present invention to train a prediction model with HTR-SELEX data to evaluate the RNA sequence preference of TAF15. Due to computational power, both positive and negative sequences are randomly downsampled to 100,000 sequences. In order to find the best model, the present invention considers three key parameters of gkm-SVM: l, the length of the entire word includes spaces; k, the number of positions of information (i.e. no gaps) in each word; d, the maximum allowed Number of mismatches. The present invention uses 5-fold cross-validation for parameter combination search. When l=7, k=3, and d=4, the highest accuracy of cross-validation is 87.3%. Finally, the present invention uses the best model to score all 7-mers occurred in XIST, and draw a smooth gkm-SVM prediction score along the XIST transcript.

FIGS. 9a to 9f show the functional verification of TAF15 and SNF2L on XCI, wherein:

FIG. 9a shows that the cells are fixed with 3% PFA solution and then stained with DAPI. The GFP signal is observed on the fluorescence microscope under the FITC channel.

FIG. 9b shows verification of shRNA knockdown efficiency. The iMEF cells are infected with the lentivirus carrying the indicated shRNA. The gene expression level is detected by RT-qPCR. β-actin is used to normalize RNA expression under different conditions. Data is expressed as mean±SD, n=3, ** p<0.01, unpaired Student's t-test.

FIG. 9c shows the TAF15 knockdown recovery experiment. The packaged Taf15 specific shRNA (shTaf15-44) and anti-shRNA Taf15 virus are used to infect iMEF cells. The expression level of Taf15 is detected by RT-qPCR, and β-actin is used as an internal control. Data is expressed as mean±SD, n=3, unpaired Student's t-test.

FIG. 9d shows the replenishing X-linked GFP suppression phenotype. The GFP expression is determined by RT-qPCR under the same experimental conditions as in Figure c. Data is expressed as mean±SD, n=3, unpaired Student's t-test.

FIG. 9e shows the role of TAF15 in the transcription of mouse autosomal genes. Two different shRNA constructs (shTaf15-07 and shTaf15-44) are used to knock out TAF15 in female iMEF cells (E2C4), similarly as shown in FIG. 1. Five autosomal genes are randomly selected from different chromosomes over 2 hours. The expression level is determined by RT-qPCR and normalized to β-actin. Data is expressed as mean±SD, n=3, *p<0.05, **p<0.01, unpaired Student's t-test, ns=not significant. FIG. 9e further shows that allelic RNA-seq is used to demonstrate the effect of TAF15 on XCI. Genes that showed significant changes in allelic expression after 5-aza treatment (NT+5-aza vs. NT) are grouped into X chromosome (chrX) genes and autosomal genes. By defining the expression ratio between the minor and major alleles before processing as 0 (unbalanced), and setting the expression ratio of the minor and major alleles after processing as 1 (balance), the allele ratios of Taf15 gene knockout for X chromosome (blue) gene and autosomal gene (grey) are summarized respectively. Data is expressed as mean±SE, and data points for a single gene measured in two biological replicates are shown. P value is calculated using unpaired Student's t test.

FIG. 9f shows a working model of the dual role of XIST lncRNA in mediating XCI.

FIGS. 10a to 10d show the CARPID results of lncRNA DANCR, wherein:

FIG. 10a is a scatter diagram showing the comparison of gene expression levels in wild-type HEK293T cells or HEK293T cells transfected with pre-gRNA expression plasmids in CARPID experiments. The x-axis represents the gene expression level after log 2 conversion of HEK293T cells in the treatment group. The y-axis represents the gene expression after log 2 conversion in wild-type HEK293T cells. The expression levels of XIST, DANCR and MALAT1 are highlighted in red. Note that MALAT1 is abundant in HEAT293T cells, and the expression level of DANCR is much lower than XIST and MALAT1.

FIG. 10b shows the location of the gRNA group of DANCR used in CARPID (upper: DANCR-L1/2; lower: MALAT1-L1/L2) and qPCR primers (upper: DANCR: P1/P2; lower: MALAT1: P1/P2). F, forward primer; R, reverse strand primer. The number in parentheses indicates the position of the gRNA set starting from 1 nt in the corresponding RNA transcript.

FIG. 10c shows that LncRNA DANCR combines proteomic identification with CARPID and then MS. The volcano map shows that in HEK293T cells expressing BASU-dCasRx, the enrichment of lncRNA DANCR-related proteins in each group of gRNA exceeds that of the control (empty gRNA expression vector). The x-axis represents the logarithmic change fold of the protein level in CARPID of each group of DANCR gRNA relative to the control. The y-axis shows the negative log 10 converted p-value after (non-parametric rank product test). Significantly enriched proteins are marked with orange dots.

FIG. 10*d* shows the top six important gene ontology (GO) term of DANCR-related proteins.

FIGS. 11*a* to 11*d* show verification of the presence of DANCR in exosomes, wherein:

FIG. 11*a* is a schematic diagram of the isolation of exosomes from cultured human cells. The exosomes used for DANCR detection are highlighted in red font.

FIG. 11*b* shows the purification of exosomes is examined by immunoblotting. 5 µg or 10 µg cell lysates and exosomal fractions are separated on SDS-PAGE gels, and subjected to Western blot analysis for the indicated proteins. Note that CD81 is highly enriched in purified exosomes.

FIG. 11*c* shows the comparison of DANCR levels in cell lysates and exosomes. Total RNA is extracted from whole cell lysates and exosomes of HEK293T cells, and DANCR transcription levels are quantified by reverse transcription followed by qPCR. Two sets of qPCR primers are used. The y-axis represents the relative content of DANCR RNA in isolated exosomes (Exosome) or whole cell lysate (Cell Lysate), expressed as an equivalent amount of total RNA. The p-value is calculated using the unpaired student's t-test. Note that DANCR is enriched in exosomes relative to whole cell lysates.

FIG. 11*d* shows the comparison of XIST levels in HEK293T whole cell lysate and exosomes. Total RNA is extracted from whole cell lysates and exosomes. Then, the same amount of RNA is reverse transcribed into cDNA for the following qPCR analysis. XIST: P1/P2 represents two different sets of qPCR primers used for XIST detection. The p value is calculated using the unpaired Student's t test.

FIGS. 12*a* to 12*b* show the CARPID results of MALAT1, wherein:

FIG. 12*a* shows that formaldehyde-assisted RIP assay is used to verify the XIST-Ezrin interaction in HEK293T cells with Ezrin antibody and IgG as controls. RT-qPCR quantitative enrichment is performed by using DANCR in two different regions and MALAT1 in two different regions. GAPDH is used as an internal control in the experiment. Data is expressed as mean±SD, n=3; ** indicates p<0.01 using the unpaired Student's t test. The upper right panel shows the abundance of Ezrin in the input sample and in the immunoprecipitation, followed by Western blotting using Ezrin antibody or IgG.

FIG. 12*b* shows the identification of the MALAT1-related proteome associated with CARPID. The volcano plot shows the enrichment of MALAT1 related proteins in HEK293T cells. The x-axis represents the log 2 transformation value of the protein level fold change in the CARPID results of all three groups of XIST gRNAs in compared with the control. The y-axis shows the negative logarithmic converted p-value (non-parametric rank product test). Significantly enriched proteins are marked with orange dots.

DETAILED DESCRIPTION OF THE INVENTION

The technical solutions of the present invention are now described in detail below for a better understanding of the technical features, objectives, and advantageous effects of the present invention, but they should not be interpreted as limiting the scope of the present invention. The experimental methods without specifying specific conditions in the examples are conventional means and conventional conditions well known in the art, or according to the conditions recommended by the manufacturer.

Example 1. Establishment of CARPID Technology

Figure 4A:
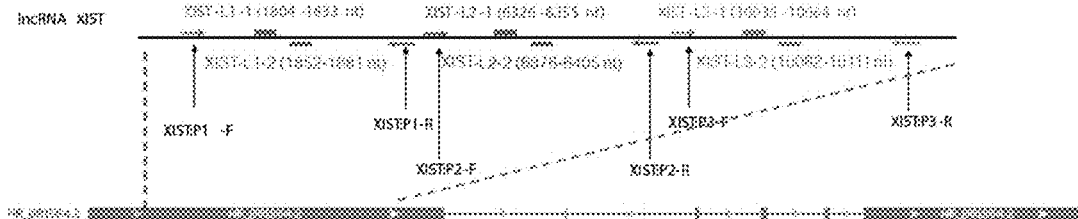

Referring to FIG. 1*a*, the present invention provides a method called CRISPR-assisted RNA-protein interaction detection (CARPID), which can be used to detect RBP bound to endogenous lncRNA transcripts in living cells. The present invention designs a guide RNA (gRNA) array, which is composed of two gRNA sequences separated by a 30 nt direct repeat (DR) to target two adjacent loci on same lncRNA transcript (FIG. 4*a*). In theory, this can improve targeting specificity, thereby reducing background noise.

Figure 4B:
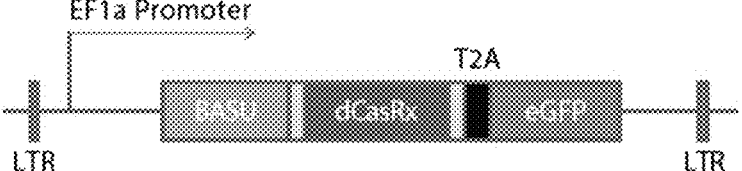
Figure 4C:
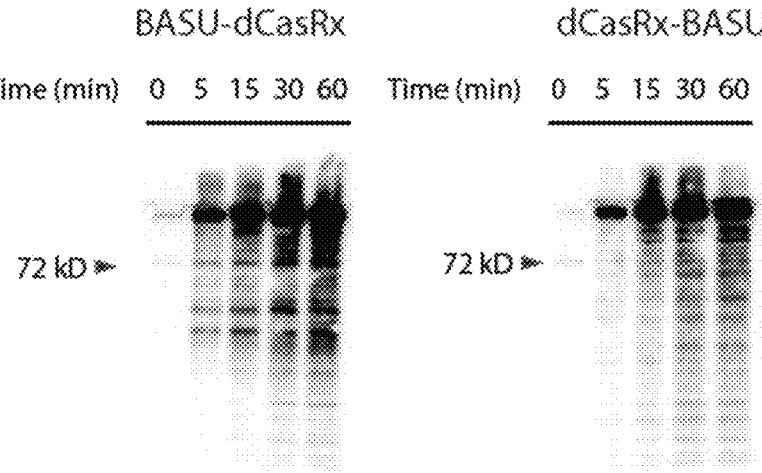
Figures 4D, 4E, 5:
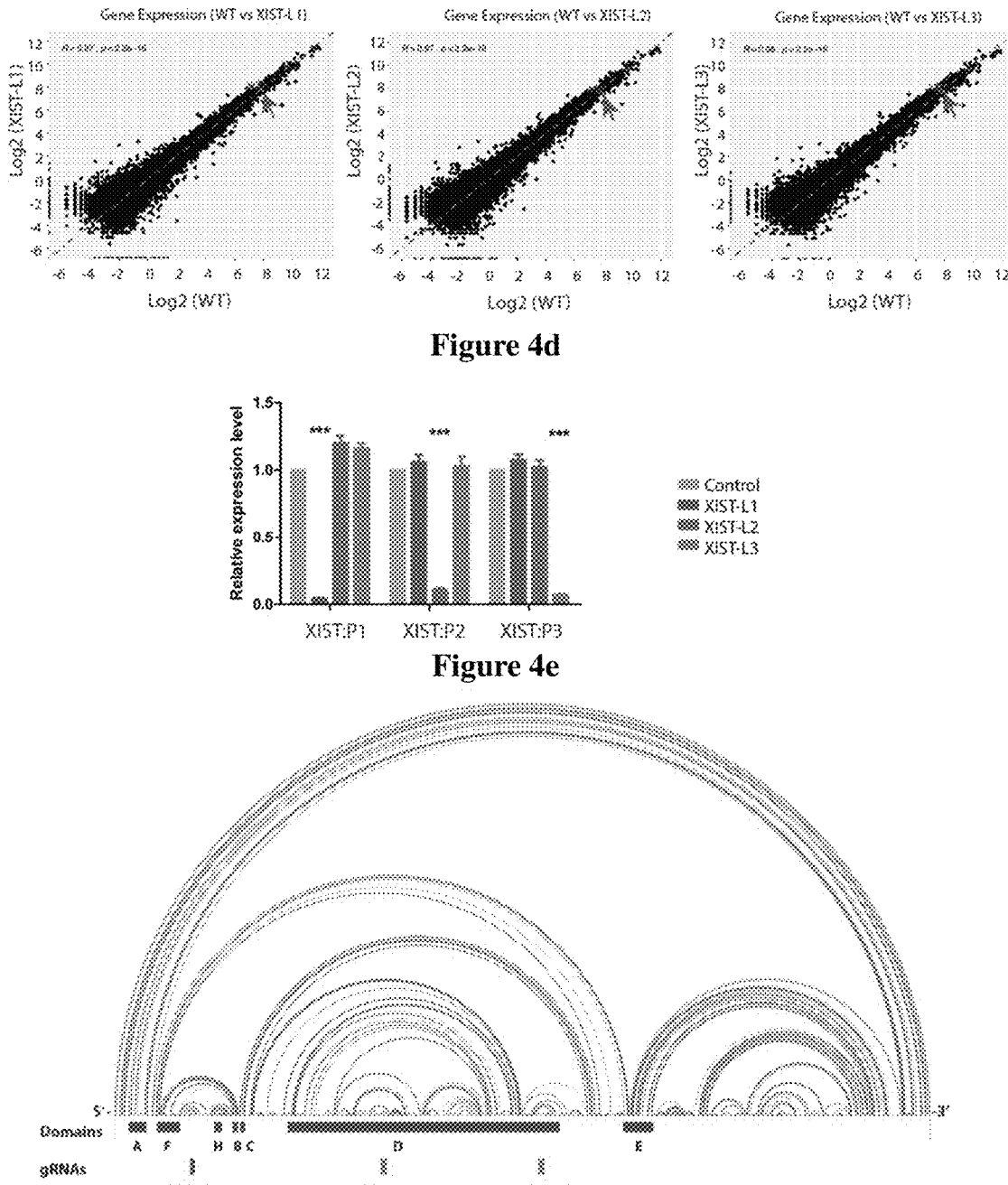

In order to identify the RBP that binds to the target lncRNA, dCasRx is fused with the engineered biotin ligase BASU in the present invention. In order to monitor and minimize the changes caused by the heterogeneous expression of BASU enzymes between cells, BASU-dCasRx is cloned in reading frame with self-cleaving T2A peptide and eGFP cDNA (FIG. 4*b*) in the present invention. In order to optimize the reaction conditions, various induction times are tried (FIG. 4*c*). The present invention also compares the enzymatic activity by reversing the order of BASU and dCasRx in the fusion protein, and no obvious difference is observed (FIG. 4*c*). The present invention selects BASU-dCasRx, and the cells are treated with 200 µM biotin for 15 minutes in the subsequent analysis, as the shortest but sufficient reaction time. By co-expressing BASU-dCasRx fusion protein with gRNA targeting specific regions of lncRNA (XIST), biotinylation is induced and then biotinylated proteins are enriched for mass spectrometry-mediated protein identification and quantification (FIG. 1*a*), so as to carry out the CARPID. No significant changes in gene expression are observed in cells overexpressing BASU-dCasRx and gRNA, confirming that CARPID does not change the physiological functions of transfected cells (FIG. 4*d*).

Example 2. Performance Evaluation of CARPID

XIST is one of the most interesting and intensively researched mammalian lncRNA genes. It is located on the long (q) arm of the X chromosome in the human genome and is only expressed in the inactive X chromosome (Xi) to regulate cis-XCI in differentiated female cells. Technical research has revealed a variety of XIST binding proteins in the art and gradually revealed potential molecular pathways. This example focuses on XIST to evaluate the performance of CARPID.

HEK293T cells are transfected with a vector expressing BASU-dCasRx and three different gRNAs targeting different regions of XIST in the present invention (FIG. 1*b*; see Table 1 for the three groups of gRNA).

TABLE 1

| | |
|---|---|
| XIST L1-1 | TGAAAAGACCTTGAAAACACCTGGTGTACC (SEQ ID No. 1) |
| XIST L1-2 | AGGAGGGGACAAATAAGAGGGGACAGAGGT (SEQ ID No. 2) |

TABLE 1-continued

| XIST L2-1 | TATGTGGAGAGGACCCTCCTTTTCTAGTGC (SEQ ID No. 3) |
| XIST L2-2 | AGTCTTATGGAGTGGGCACTCCCTGCTGGA (SEQ ID No. 4) |
| XIST L3-1 | AGTAGAGGGGTTCATGTATAATGGGTGGGA (SEQ ID No. 5) |
| XIST L3-2 | AGAAGGGGCTTTGGGTAGTCAGCATACTCA (SEQ ID No. 6) |
| DANCR L1-1 | TAAGAGACGAACTCCTGGAGCTCAAGGTCG (SEQ ID No. 7) |
| DANCR L1-2 | GCTGCCTCAGTTCTTAGCGCAGGTTGACAA (SEQ ID No. 8) |
| DANCR L2-1 | TTCCTATTGTAACTGAAGGGATAGTTGGCT (SEQ ID No. 9) |
| DANCR L2-2 | CCAAATATGCGTACTAACTTGTAGCAACCA (SEQ ID No. 10) |
| MALAT1 L1-1 | AGTTGCGGGGCCCCAGTCCTTTACAGAAGT (SEQ ID No. 11) |
| MALAT1 L1-2 | TTCTGCGTTGCTAAAATGGCGCTGCGCTTA (SEQ ID No. 12) |
| MALAT1 L2-1 | AATCTTAGAAACGTGAAAACCCACTCTTGG (SEQ ID No. 13) |
| MALAT1 L2-2 | TTGCTTTTTTGTTCGAGAAATCGGAGCAGC (SEQ ID No. 14) |

The specificity of these gRNA groups is confirmed by co-transfection with active CasRx, the CasRx co-transfection shows that the target area is specifically digested without affecting other areas (FIG. 4e). Due to the highly ordered structure of XIST, the present invention also avoids targeting the expected XRNA hairpin structure (FIG. 5).

Figures 6A, 6B, 6C:
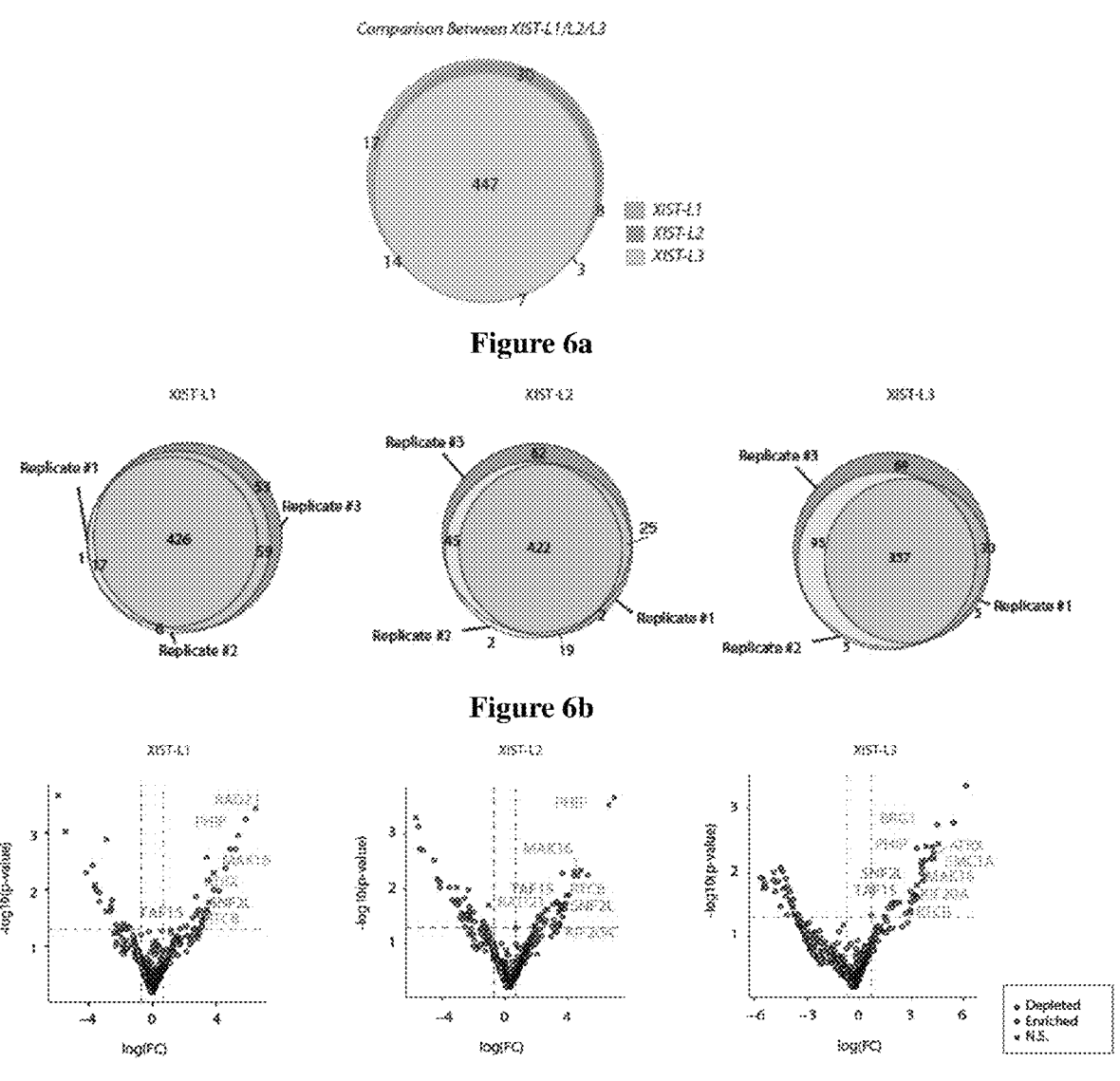

Three biological repetitions for each group of gRNA are performed in the present invention to further "dilute" the non-specific noise generated by random binding. To determine the baseline of background biotinylation, an empty gRNA vector is used in the present invention to perform a control CARPID. The protein identification based on mass spectrometry (MS) shows that most of the detected proteins with at least two peptides (447 proteins) are shared between different gRNA groups and in triplicate of each group, which indicates that CARPID has strong repeatability (FIG. 6a, FIG. 6b).

For the enrichment analysis, label-free MS quantitation and non-parametric rank product test are applied in the present invention, the enrichment cut-off value is >2 times, and the adjusted p value is <0.05. The results show that at least one group of gRNA significantly enriched in 73 XIST interaction proteins compared with the vector control group (FIG. 1c). In addition, 23 of the 73 proteins are found to have at least two different groups of gRNAs, and 13 of which are shared by all three gRNA pairs (FIG. 1d; FIG. 6c). Previous studies have reported more than a quarter (19/73) of these strong XIST interaction proteins (FIG. 1d), including a variety of functionally verified conjugates: Cohesin subunits RAD21 and SMC1A, an ATP-dependent helicase ATRX, SWI/SNF chromatin remodeling agent BRG1. It is also noted in the present invention that some known XIST interactive RBPs, such as SPEN and RBM15, are not in this list. The inventors believe that their binding to XIST may be weak or dynamic in living cells, and are difficult to enrich.

Gene ontology (GO) analysis of significantly enriched candidate proteins shows that the proteins interacting with XIST are largely involved in covalent chromatin modification and chromatin remodeling (FIG. 1e). The ATP-dependent helicase ATRX found in CARPID belongs to these categories. This gene is also reported in an independent study, asserting that it played a role in guiding the polycomb complex PRC2 to the X chromosome for inactivation and gene silencing. These findings of the present invention strongly indicate that CARPID is a highly reliable method for determining RBP.

Figure 2E:
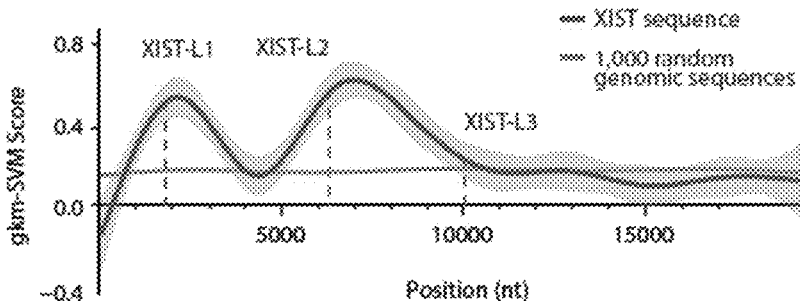
Figure 8C:
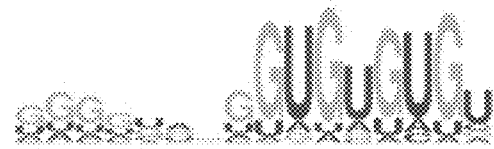
Figure 8D:
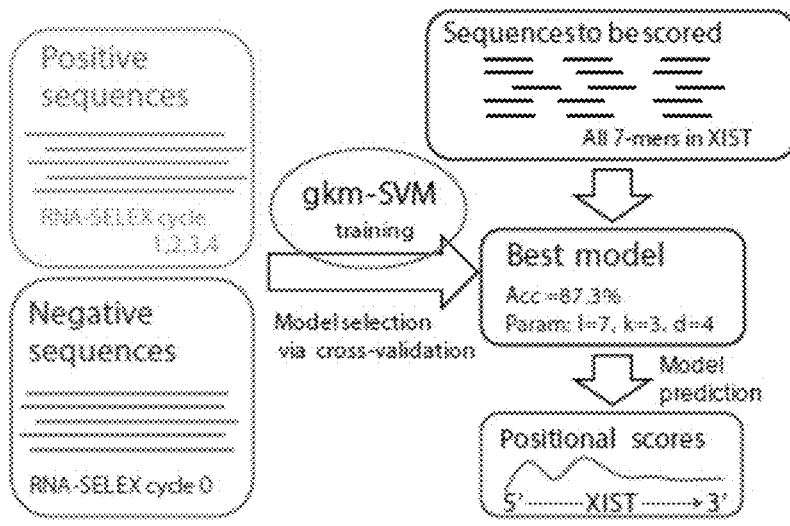

In addition to the known XIST interactors, CARPID has also identified a variety of new factors, including the transcription initiation factor TFIID subunit TAF15 (FIG. 1c, FIG. 1d). TAF15 is known to interact with TATA-box binding protein (TBP) and RNA polymerase II, and act as a co-activator that recognizes the core promoter and promotes transcription initiation. The present invention firstly confirms the association between TAF15 and XIST lncRNA by Western blotting (WB) and immune FISH (FIG. 2a, FIG. 7). It is reported that TAF15 is an RNA binding protein in mouse tissues. Therefore, the present invention re-studies the TAF15 CLIP-seq data in the mouse brain, and found that TAF15 does significantly bind to XIST lncRNA, and the binding cluster enrichment degree exceeded the expected 9 times (FIG. 2b, FIG. 2c). In order to study whether the binding of TAF15 depends on its biochemical binding affinity to XIST lncRNA sequence characteristics, a library containing 40-nt RNA transcripts and random sequences is used in the present invention to perform HTR-SELEX experiments on TAF15 (FIG. 8a, FIG. 8b). HTR-SELEX identified significant enrichment of RNA sequence motifs of TAF15 (FIG. 8c), similar to previous reports. Given that the abundant hairpin structure in XIST lncRNA may lead to dinucleotide interdependence, the effect of RNA sequence on TAF15 binding cannot be fully described by a simple position weight matrix model. Therefore, a k-mer-based machine learning algorithm (gkm-SVM) is used in the present invention, and HTR-SELEX data is used to model the RNA binding specificity of the human TAF15 protein (FIG. 8d). Consistent with the WB and MS results, the HTR-SELEX results further support that the affinity of locus 1 and 2 where TAF15 binds to XIST lncRNA is higher than locus 3 (FIG. 2e).

The well-studied chromatin remodeling agent SNF2L is also found in CARPID (FIG. 1c), and confirmed by WB and immune FISH (FIG. 20. Consistently, the RIP-qPCR results shows that XIST lncRNA is significantly correlated with SNF2L (FIG. 2g). SNF2L and SNF2H are two collateral ATP-dependent chromatin remodeling enzymes belonging to the ISWI (Imitation Switch) family, which can move nucleosomes along DNA. For more than ten years, IWSI has been known to be associated with cohesin complexes in human cells. Consistent with this, the present invention identified two cohesin subunits SMC1A and RAD21 that interact with XIST (FIG. 1c).

Figure 2H:
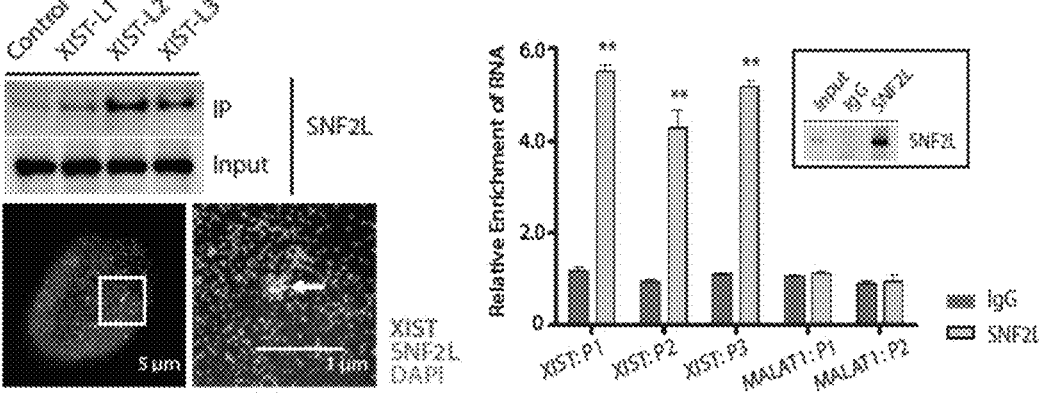
Figure 2H:
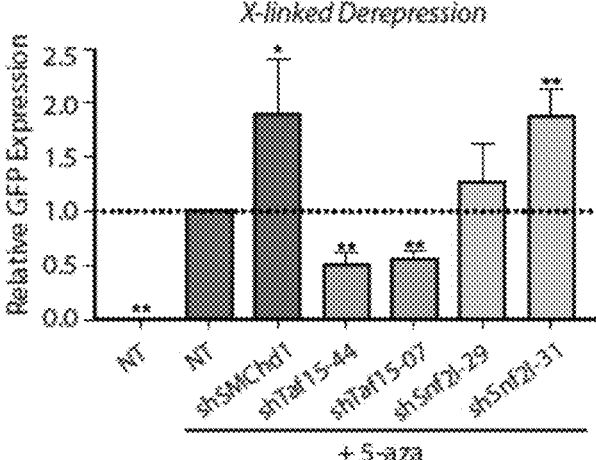
Figure 9A:
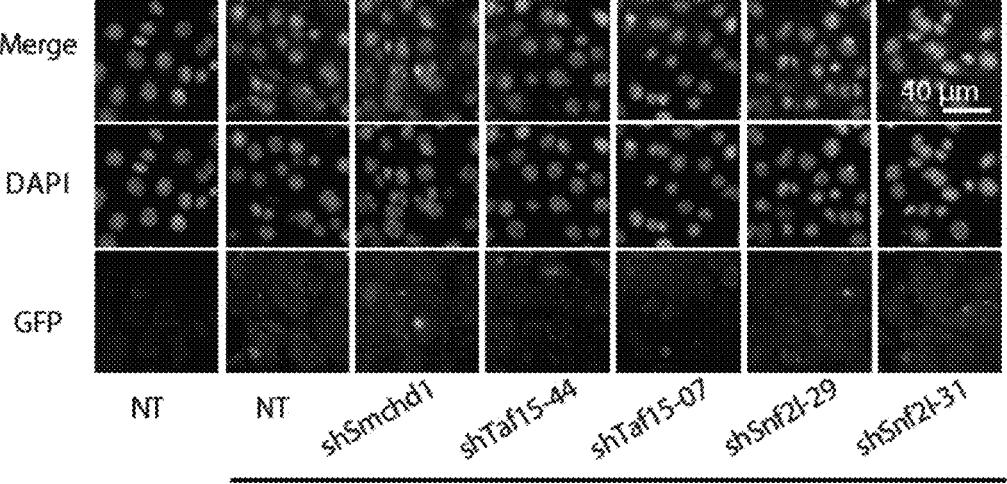
Figure 9B:
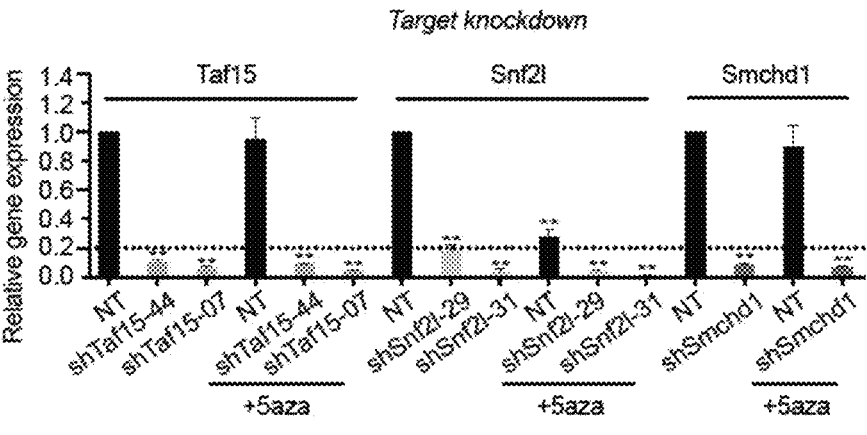
Figure 9C:
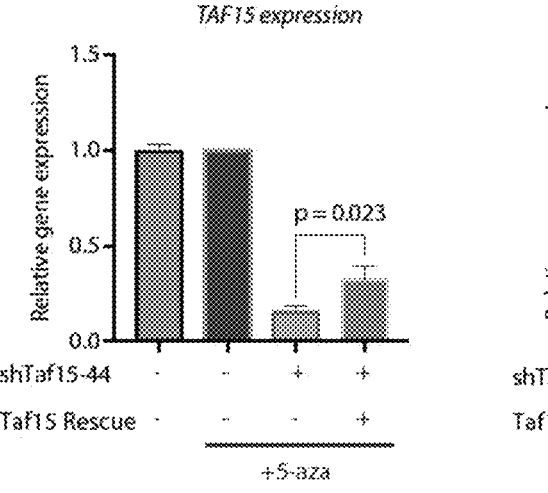
Figure 9D:
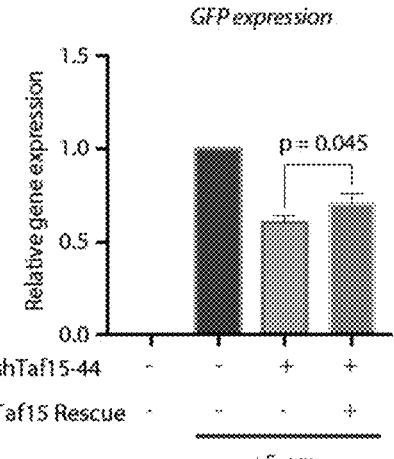
Figure 9E:
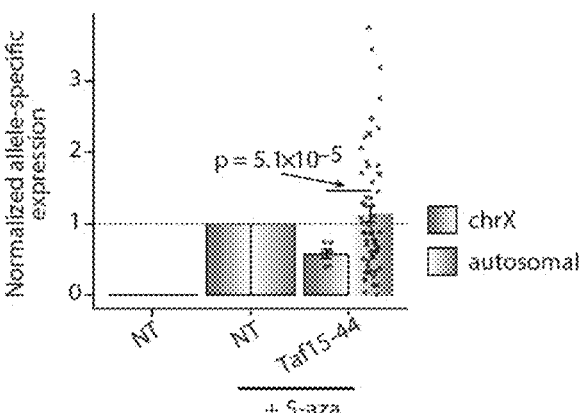

In order to verify the role of these two new RBPs in mammalian XCI, a transgene female mouse embryonic fibroblast cell line with Xi-linked GFP reporter gene is used in the present invention. Xi-linked GFP is silenced by multiple epigenetic mechanisms. Therefore, no GFP transcript is detected (FIG. 2h) and no fluorescent signal is observed (FIG. 9a). In contrast, when 5'-azacytosine (5-aza) is used to inhibit DNA methylation, both GFP mRNA and fluorescence signal increased significantly. In order to clarify their functional importance in XCI, TAF15 and SNF2L are depleted in the presence of 5-aza processing in the present invention (FIG. 9b). Surprisingly, after silencing TAF15, the level of 5-aza-enhanced GFP is significantly reduced, which can be partially rescued by ectopic expression of RNAi-resistant TAF15 cDNA (FIG. 9c, FIG. 9d). In order to rule out the possibility that TAF15-related XCI is specific to the knocked-in GFP locus, RNA sequencing is performed in the present invention after the exhaustion of TAF15 in the female mouse embryonic fibroblast cell line under the genetic background of MAF and Cast hybrid. The allelic expression of a gene can be determined by the availability of SNPs between two different genetic backgrounds. As expected, the genes on the X chromosome show greater allelic depletion than autosomal genes (FIG. 9e), which proves the role of TAF15 in antagonizing XCI. On the other hand, in 5-aza-treated cells, knockdown of SNF2L resulted in further suppression of GFP (FIG. 2h, FIG. 9a), indicating that SNF2L and XIST RNA act synergistically to promote XCI.

Figure 9F:
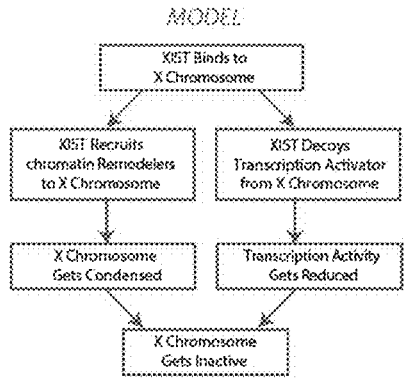

Functionally, SNF2L and TAF15 belong to transcription repressor and activator, respectively. The present invention found that SNF2L is used as XIST RBP, indicating that ISWI family proteins may promote XCI through their known function of regulating the higher-order structure of chromatin. The binding of TAF15 and XIST indicates that XIST RNA can repel TAF15 and possibly other transcriptional activators from binding to the promoter of Xi-linked genes, thereby preventing the expression of target genes. This phenomenon supports a multitasking model that recruits inhibitors (such as SNF2L) and expulsion transcription activators (such as TAF15), and they may be the basis of XIST-mediated X chromosome inactivation (FIG. 9f).

Example 3. Application of CARPID

Figure 10A:
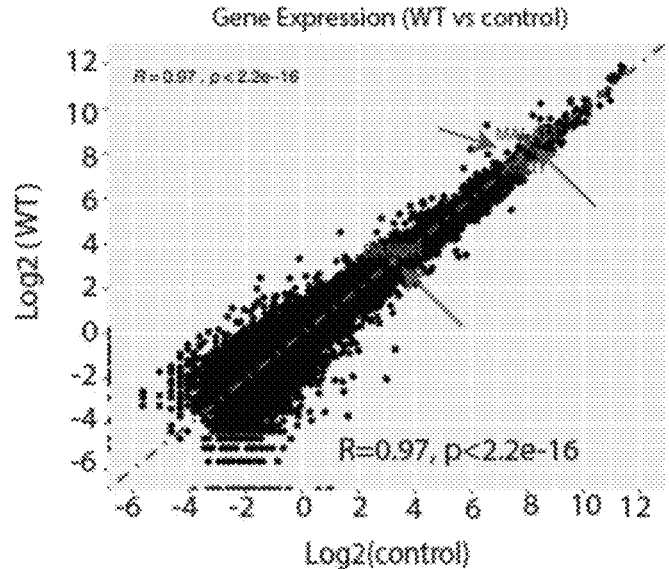

In order to generalize the application of CARPID and extend its application to non-nuclear lncRNAs, the present invention designs a gRNA set with respect to two other lncRNAs DANCR (differentiation antagonistic non-protein coding RNA) and MALAT1 (lung adenocarcinoma transcript 1 associated with metastasis). It is reported that DANCR transcripts mainly exist in the cytoplasm, and their overexpression is significantly related to the poor prognosis of a variety of cancers, including breast cancer, liver cancer, colorectal cancer and osteosarcoma. However, the molecular mechanism has not yet been elucidated. It is important to note that the length of DANCR is 1000 nucleotides, which is much shorter than XIST. This and its low abundance in cells (FIG. 10a) make it technically challenging to conduct research using currently available methods (such as ChIRP-MS), which requires spanning dozens of different RNA probes in order to sufficiently capture.

Figure 3A:
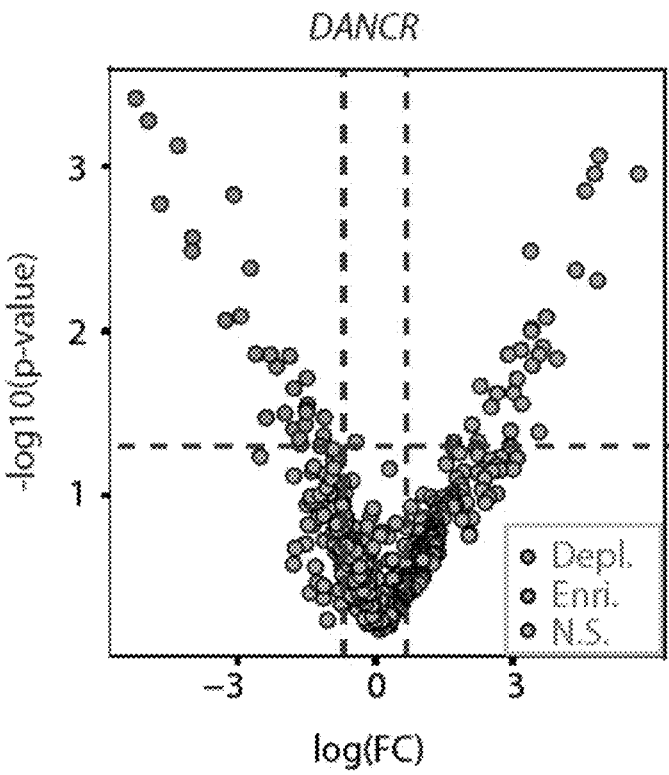
Figure 3B:
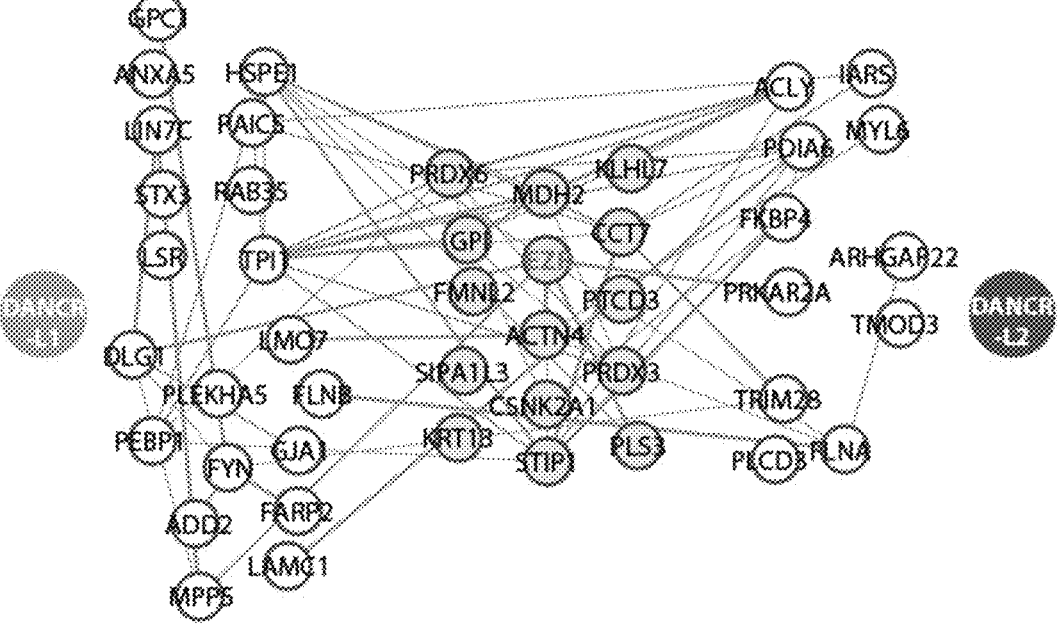
Figure 10B:
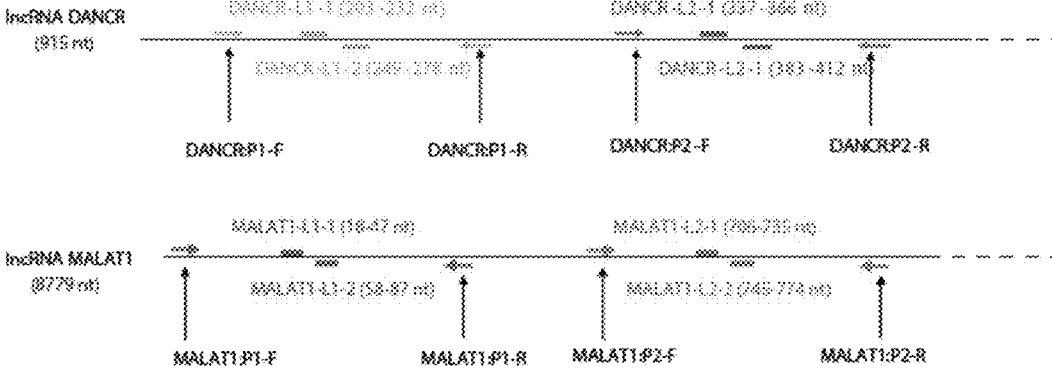
Figure 10C:
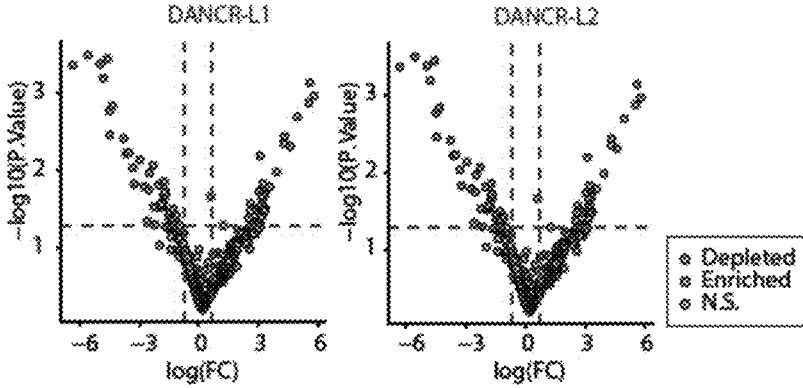

CARPID is used together with two sets of gRNA in HEK293T cells (FIG. 10b), and the present invention detects 640 DANCR lncRNA-related proteins (≥2 peptides), of which 35 and 26 proteins are significantly enriched in the locus 1 and locus 2 (FIG. 3a, FIG. 3b, FIG. 10c).

Figure 11C:
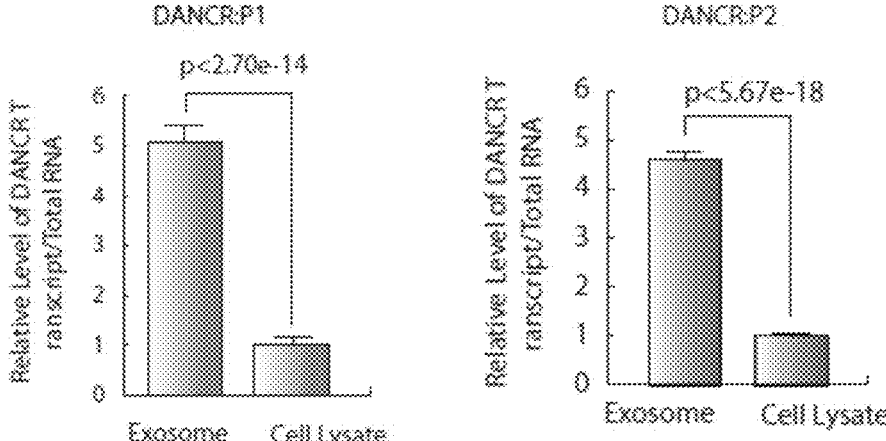
Figure 11D:
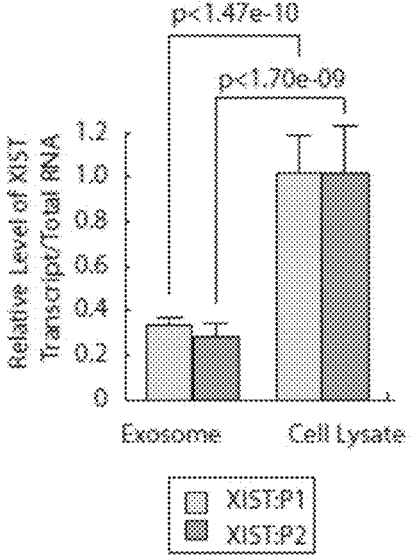
Figure 12A:
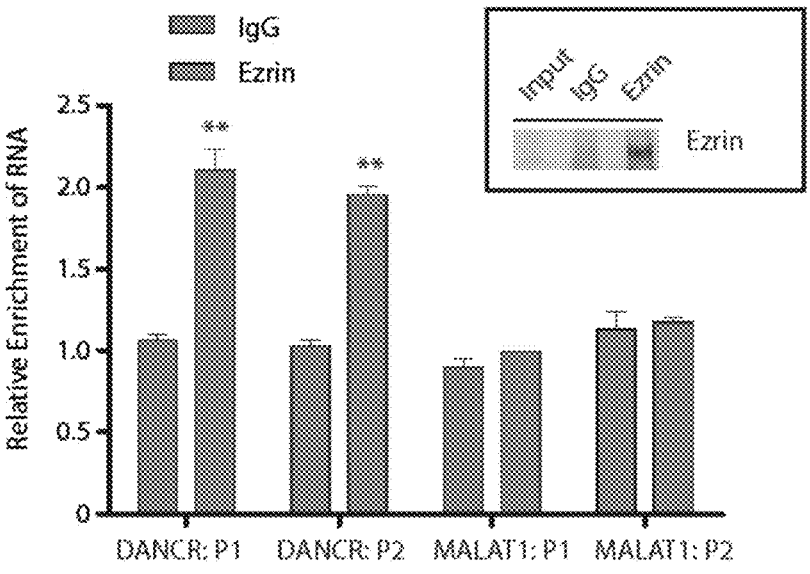

It is worth noting that GO-term analysis shows that most DANCR-related proteins are rich in extracellular vesicles, which indicates that DANCR is located in this specialized cell compartment (FIG. 10d). To verify this, the present invention purifies vesicles from HEK293T cells and checks the total RNA of exosomes and whole cell lysates (FIG. 11a, FIG. 11b). Indeed, quantitative RT-PCR analysis shows that the degree of enrichment of DANCR in exosomes is 5 times that of cell lysates (FIG. 11c). In contrast, XIST is largely consumed in exosomes (FIG. 11d). The present invention also notes an interesting DANCR binding protein Ezrin (EZR) (FIG. 10d), a membrane-bound cytoskeleton junction protein, which is associated with the poor prognosis of many cancers. RIP-qPCR verified the binding of Ezrin to DANCR lncRNA. Compared with the IgG control, DANCR lncRNA is approximately 2 times enriched in the Ezrin drop-down list, but it is not used for MALAT1 lncRNA (FIG. 12a).

Figure 3C:
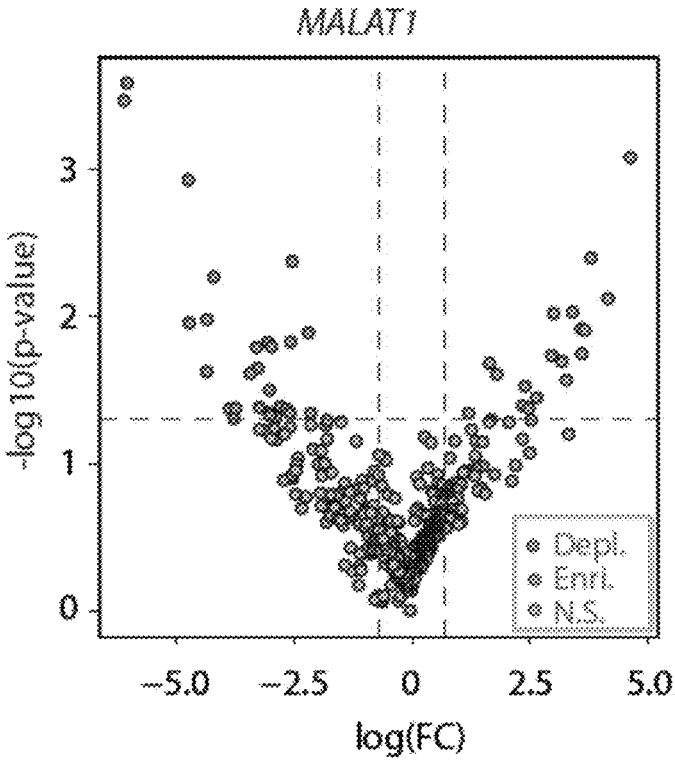
Figure 3D:
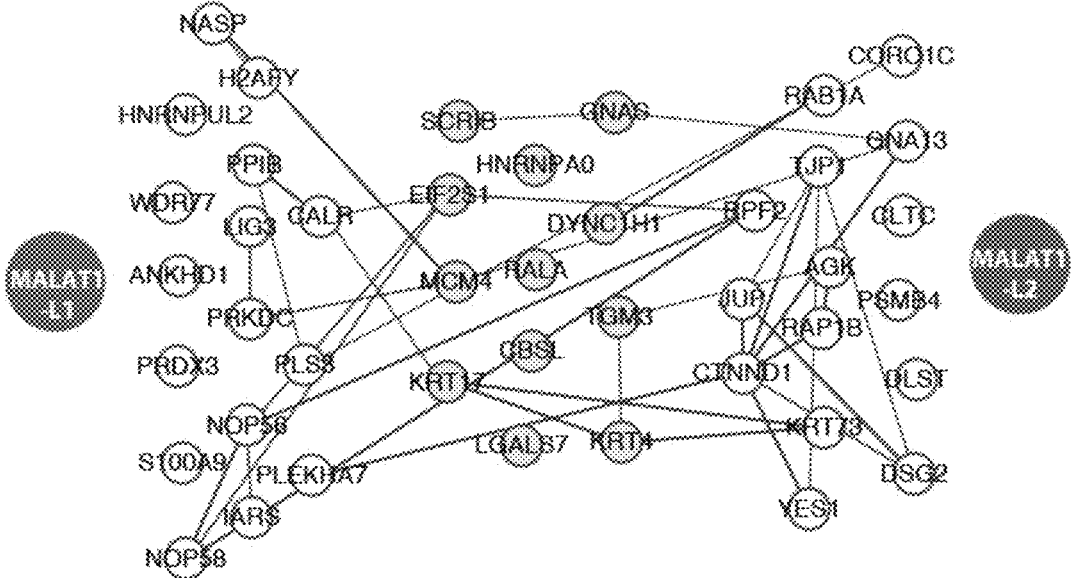
Figure 12B:
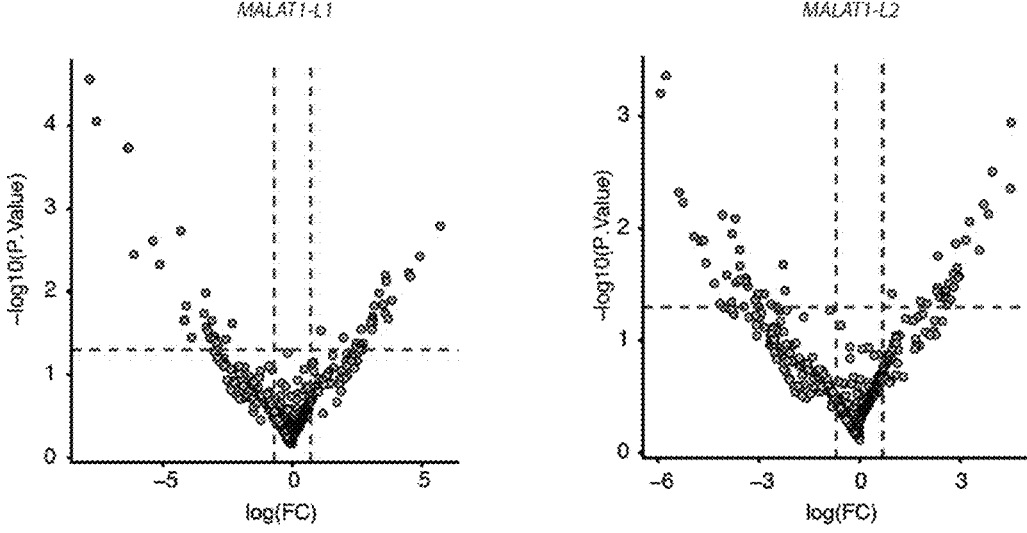

CARPID is also performed in the present invention on another lncRNA MALAT1 that is known to be abundant in the nucleus but also present in the cytoplasm. Two groups of different gRNAs used for human MALAT1 can capture 484 proteins (≥2 peptides), of which 43 proteins are significantly enriched (FIG. 3c, FIG. 3d, FIG. 12b).

Figure 3E:
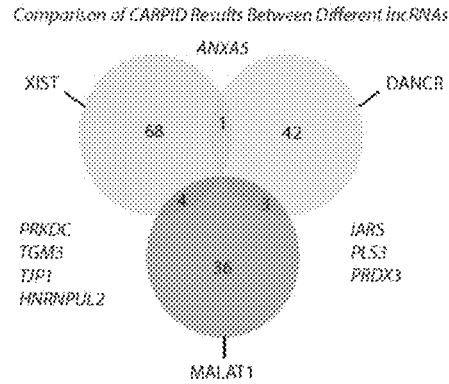

In this study, among the three tested lncRNAs, the comparison results of CARPID that partially share the subcellular distribution results in the candidates with almost no overlap, demonstrating the high specificity of the CARPID method (FIG. 3e). In summary, these data support that CARPID is a powerful tool for studying lncRNAs of various lengths and expression levels in various subcellular locations.

Each document, reference, patent application or patent cited in this text is expressly incorporated herein in their entirely by reference, which means that it should be read and considered by the reader as part of this text. That the document, reference, patent application, or patent cited in this text is not repeated in this text is merely for reasons of conciseness.

---

The invention claimed is:

1. A fusion protein formed by biotin ligase BASU and dCasRx, said fusion protein selected from the group consisting of *B. subtilis* biotin ligase with C-terminal mutation (BASU) as encoded by SEQ ID NO: 17-dCasRx as encoded by SEQ ID NO: 18 and dCasRx as encoded by SEQ ID NO: 18-BASU as encoded by SEQ ID NO: 17.

2. A composition comprising:

the fusion protein according to claim 1; and a pair of guide RNAs (gRNA) targeting a target long non-coding ribonucleic acid (lncRNA).

3. A kit for determining lncRNA interaction proteins, comprising:

the fusion protein according to claim 1; and a gRNA set targeting a target lncRNA.

4. The composition according to claim 2, wherein the target lncRNA is selected from the group consisting of X-inactivation specific transcript (XIST), Differentiation antagonizes non-protein-coding RNAs (DANCR), and Metastasis Associated Lung Adenocarcinoma Transcript 1 (MALAT1).

5. The kit according to claim 3, wherein the kit further comprises:

a control reagent without gRNA.

* * * * *